US008487109B2

(12) United States Patent
Rkyek et al.

(10) Patent No.: US 8,487,109 B2
(45) Date of Patent: Jul. 16, 2013

(54) PROCESS FOR THE PALLADIUM-CATALYZED COUPLING OF TERMINAL ALKYNES WITH ARYL TOSYLATES

(75) Inventors: Omar Rkyek, Kassel (DE); Marc Nazare, Frankfurt am Main (DE); Andreas Lindenschmidt, Frankfurt am Main (DE); Matthias Urmann, Frankfurt am Main (DE); Nis Halland, Frankfurt am Main (DE); Jorge Alonso, Mannheim (DE)

(73) Assignee: Sanofi, Paris (FR)

( * ) Notice: Subject to any disclaimer, the term of this patent is extended or adjusted under 35 U.S.C. 154(b) by 610 days.

(21) Appl. No.: 12/645,509

(22) Filed: Dec. 23, 2009

(65) Prior Publication Data
US 2010/0261910 A1    Oct. 14, 2010

Related U.S. Application Data

(63) Continuation of application No. PCT/EP2008/004927, filed on Jun. 19, 2008.

(30) Foreign Application Priority Data

Jul. 3, 2007 (EP) .................................. 07290840

(51) Int. Cl.
| C07D 211/60 | (2006.01) |
| C07D 333/22 | (2006.01) |
| C07C 229/38 | (2006.01) |
| C07C 45/00 | (2006.01) |
| C07C 233/03 | (2006.01) |

(52) U.S. Cl.
USPC .............. 546/230; 549/77; 560/41; 564/218; 564/221; 568/319

(58) Field of Classification Search
CPC ...... C07D 211/60; C07D 333/22; C07C 45/00; C07C 233/03; C07C 229/38
USPC ............ 546/230; 548/77; 560/41; 564/218; 564/221; 568/319
See application file for complete search history.

(56) References Cited

U.S. PATENT DOCUMENTS 7,560,596 B2 *  7/2009  Buchwald et al. .............. 568/13
2006/0069257 A1   3/2006  Buchwald et al.

OTHER PUBLICATIONS

Adjabeng, G. M. "Phospha-adamantanes as Ligands for Palladium-Catalyzed Cross-Coupling Reactions." M.Sc. Thesis, Dept. of Chemistry, Brock University, 2003.*
Gelman, Dmitri et al., "Efficient Palladium-Catalyzed Coupling of Aryl Chlorides and Tosylates with Terminal Alkynes: Use of a Copper Cocatalyst Inhibits the Reaction," Angewandte Chemie International Edition (2003), vol. 42, pp. 5993-5996.
Krstenansky, John L. et al., "Recent advances in microwave-assisted organic syntheses," Current Opinion in Drug Discovery and Development (2000), vol. 3, No. 4, pp. 454-461.
Philip, Philip A. et al., "Phase II Study of Erlotinib in Patients With Advanced Biliary Cancer," Journal of Clinical Oncology (2006), vol. 24, No. 19, pp. 3069-3074.
Tsuji, Jiro, "Palladium in Organic Synthesis. Topics in Organometallic Chemistry, 14," Journal of the American Chemical Society (2006), vol. 128, pp. 9574.
Veraldi, Stefano et al., "Short Contact Therapy with Tazarotene in Psoriasis Vulgaris," Dermatology (2006), vol. 212, pp. 235-237.
International Search Report dated Aug. 6, 2008 issued in PCT/EP2008/004927.

* cited by examiner

*Primary Examiner* — Joseph K. McKane
*Assistant Examiner* — Amanda L Aguirre
(74) *Attorney, Agent, or Firm* — Scully, Scott, Murphy & Presser, P.C.

(57) ABSTRACT

The present invention relates to a process for the regioselective synthesis of compounds of the formula (I),

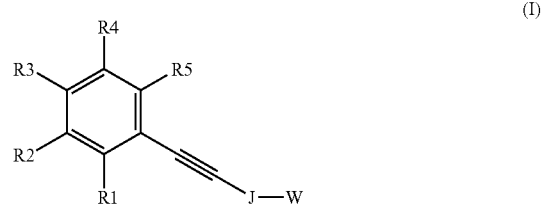

wherein R1; R2; R3; R4; R5; J and W have the meanings indicated in the claims. The present invention provides an efficient and general palladium-catalyzed coupling process for aryl tosylates with terminal alkynes to a wide variety of substituted, multifunctional aryl-1-alkynes of the formula I.

14 Claims, No Drawings

PROCESS FOR THE PALLADIUM-CATALYZED COUPLING OF TERMINAL ALKYNES WITH ARYL TOSYLATES

FIELD OF THE INVENTION

The present invention relates to a process for the regioselective synthesis of compounds of the formula (I),

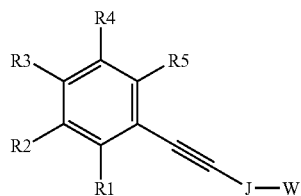

wherein R1; R2; R3; R4; R5; J and W have the meanings indicated below and which are useful as intermediates for the preparation of valuable pharmaceutically active ingredients.

BACKGROUND OF THE INVENTION

The present invention relates to an efficient and palladium-catalyzed, regioselective process for the preparation of a wide variety, of multifunctionally substituted aryl-1-alkynes of the formula (I) starting from aryl tosylates and terminal alkynes in the presence of a base, a bidentate ligand and a protic solvent.

Aryl-1-alkynes play an important role as key synthetic intermediates. The ability of the alkyne moiety of intermediates of the formula I to selectively react with various electrophiles or nucleophiles with or without catalytic assistance of acids or bases or transition metal is well known to those skilled in the art. Thus, aryl-1-alkynes are valuable synthetic precursors for a wide variety of other compound classes, like for example indoles, benzofuranes, isochinolines, benzothiophenes, isoquinolines, N-oxide isoquinolines, acetophenones, benzoic acids, aryl-alkenyls, naphthalenes, cinnolines, chromenones and isocoumarins. In addition, aryl-1-alkynes are well known as pharmaceutically active ingredients and several reports document the activity on a variety of biological targets, as well as the fact that several aryl-1-alkynes are in development or are marketed as drugs (P. A. Philip, M. R. Mahoney, C. Allmer, J. Thomas, H. C. Pitot, G. Kim, R. C. Donehower, T. Fitch, J. Picus, C. Erlichman, J. Clin. Oncol. 2006, 19, 3069-3074; S. Veraldi, R. Caputo, A. Pacifico, K. Peris, R. Soda, S. Chimenti, Dermatology 2006, 212(3), 235-237.)

The use of aryl-1-alkynes is of course not limited to the above-mentioned application. For example it is well known that aryl-1-alkynes can be useful in agricultural applications e.g. as herbicides, fungicides, nematicidals, parasiticides, insecticides, acaricides and arthropodicides. In addition they are used as diagnostic agents, liquid crystals and in polymers.

Among the synthetic repertoire for the preparation of aryl-1-alkynes, the transition metal catalyzed formation of the $C(sp)-C(sp^2)$ bond between the aryl and the alkyne moiety is by far the most commonly used strategy (J. Tsuji Palladium in Organic Synthesis. Top. Organomet. Chem.; 2005, Vol. 14, Springer Berlin). For this purpose numerous transition metal catalyzed cross-coupling methodologies between an aryl halide or aryl triflate and a organometalic alkyne involving for example a discrete zinc, tin, boron, copper, silicon species have been developed. In contrast to these methods the palladium-catalyzed and optionally copper co-catalyzed cross-coupling of an aryl halide or aryl triflate and a non-metalated terminal alkyne as precursors ("Sonogashira coupling") has turned out to be one of the most powerful and straightforward methods for the construction of aryl-1-alkynes, since terminal alkynes can be used without prior transformation into a organometalic derivative. Despite the large number of applications of the Sonogashira reaction the coupling partners of the alkyne component are aryl iodides, aryl bromides and more recently also aryl chlorides and aryl triflates.

Recently the use of aryl tosylates was reported by Buchwald et al. (Angew. Chem. Int. Ed. 2003, 42, 5993-5996). However, only three examples with a toluene-4-sulfonic acid 4-cyano-phenyl ester, a toluene-4-sulfonic acid 3-trifluoromethyl-phenyl ester and a 5-(toluene-4-sulfonyloxy)-isophthalic acid dimethylester were disclosed. No process of ortho-substituted aryl tosylates were described. Further the toxic solvent $C_2H_5CN$ was used and slow addition of the alkyne component over 8 hours to the reaction mixture is required to obtain the reported yields. Therefore, the scope of the reported process involving $PdCl_2(CH_3CN)_2$ as catalyst, dicyclohexyl[2',4',6'-tris(1-methylethyl)[1,1'-biphenyl]-2-yl]-phosphine (X-Phos) as a monodentate ligand and $Cs_2CO_3$ as base in refluxing $C_2H_5CN$ seems to be very limited.

It has now been found that the disadvantages mentioned can be avoided by a direct, catalytic, mild, versatile and regioselective synthesis for aryl-1-alkynes of formula I. The object is achieved by starting from aryl tosylates of formula II and terminal alkynes of formula III in the presence of a bidentate ligand, a palladium catalyst, a base and a protic solvent.

The addition of a bidentate ligand and the use of a protic solvent now allow the preparation of a wide variety of substituted aryl-1-alkynes of formula I. Further it is now no more necessary to slowly add the alkyne component of formula III over a long period of time.

SUMMARY OF THE INVENTION

The present invention provides an efficient and palladium-catalyzed coupling process for the preparation of aryl-1-alkynes of the formula (I) starting from aryl tosylates of the formula II with terminal alkynes of the formula III and thus provides a new synthetic route with a good time- and cost effectiveness. The addition of a bidentate ligand and the use of a protic solvent now allow the preparation of a wide variety of substituted aryl-1-alkynes of formula I.

The advantages of the present invention is a process wherein the compounds of formula I can be prepared under catalytic, mild and general reaction conditions for the synthesis of substituted aryl-1-alkynes, wherein the aryl tosylates of the formula II are easily and inexpensively obtainable from the corresponding phenols and are stable, often crystalline solids and conveniently to purify intermediates. Thus, the process is very time- and cost-effective. Moreover the reaction conditions are compatible with a broad range of functional groups and a large variety of starting materials, which are easily accessible or even commercially available.

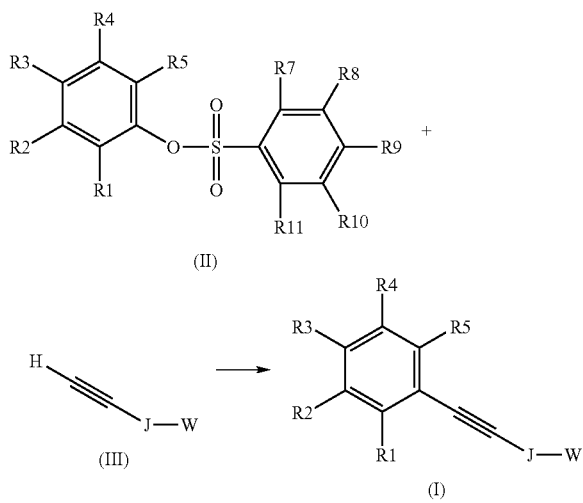

DETAILED DESCRIPTION OF THE INVENTION

The invention therefore relates to a process for preparing a compound of formula I

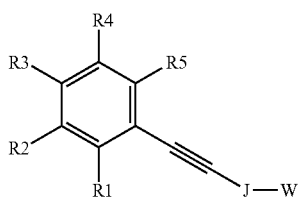

and/or all stereoisomeric forms of the compound of formula I, and/or mixtures of these forms in any ratio, and/or a physiologically tolerated salt of the compound of formula I, wherein J is a covalent bond;
—$(C_1-C_6)$-alkylene, wherein alkylene is unsubstituted or mono-, di- or trisubstituted independently of one another by R6;
—$(C_3-C_8)$-cycloalkyl, wherein cycloalkyl is unsubstituted or mono-, di- or trisubstituted independently of one another by R14;
—$(C_6-C_{14})$-aryl, wherein aryl is unsubstituted or mono-, di-, tri- or four times substituted independently of one another by R13; or
—$(C_4-C_{14})$-heteroaryl, wherein heteroaryl is unsubstituted or mono-, di-, tri- or four times substituted independently of one another by R13;

W is hydrogen atom,
—$(C_1-C_6)$-alkyl, wherein alkyl is unsubstituted or mono-, di- or trisubstituted independently of one another by R6;
—$(C_3-C_8)$-cycloalkyl, wherein cycloalkyl is unsubstituted or mono-, di- or trisubstituted independently of one another by R6;
—$(C_6-C_{14})$-aryl, wherein aryl is unsubstituted or mono-, di-, tri- or four times substituted independently of one another by R6; or
—$(C_4-C_{14})$-heteroaryl, wherein heteroaryl is unsubstituted or mono-, di-, tri- or four times substituted independently of one another by R6;

R1, R2, R3, R4, R5 and R6 are independent of one another identical or different and are
a) hydrogen atom,
b) —$(C_1-C_4)$-alkyl, wherein alkyl is unsubstituted or substituted one to three times by R13,
c) halogen,
d) phenyloxy-, wherein phenyloxy is unsubstituted or substituted one to three times by R13,
e) —$(C_1-C_3)$-fluoroalkyl,
f) —N(R15)-$(C_1-C_4)$-alkyl, wherein alkyl is unsubstituted or substituted one to three times by R13,
g) —$(C_6-C_{14})$-aryl, wherein aryl is unsubstituted or mono-, di-, tri- or four times substituted independently of one another by R13,
h) —$(C_4-C_{14})$-heteroaryl, wherein heteroaryl is unsubstituted or mono-, di-, tri- or four times substituted independently of one another by R13,
i) —$(C_3-C_8)$-cycloalkyl, wherein said cycloalkyl is unsubstituted or mono-, di-, tri- or four times substituted independently of one another by R13,
j) a 3- to 7-membered cyclic residue, containing 1, 2, 3 or 4 heteroatoms chosen from nitrogen, sulfur or oxygen, wherein said cyclic residue is unsubstituted or mono-, di-, tri- or four times substituted independently of one another by R13,
k) —O—$CF_3$,
l) —O—$(C_1-C_4)$-alkyl, wherein alkyl is unsubstituted or substituted one to three times by R13,
m) —$NO_2$,
n) —CN,
o) —OH,
p) —C(O)—R15,
q) —C(O)—O—R16,
r) —C(O)—N(R16)-R12,
s) —N(R16)-R12,
t) —N(R15)-$SO_2$—R15,
v) —S—R15,
w) —$SO_n$—R15, wherein n is 1 or 2,
x) —$SO_2$—N(R16)-R12 or
y) —Si(R16)(R16)-R12, or R1 and R2, R2 and R3, R3 and R4 or R4 and R5 form together with the atoms which they are attached to a 5- or 8-membered ring, containing up to 0, 1, 2, 3 or 4 heteroatoms chosen from nitrogen, sulfur or oxygen, wherein said ring is unsubstituted or substituted one, two, three or four times by R14, R15 is hydrogen atom, —$(C_1-C_3)$-fluoroalkyl or —$(C_1-C_6)$-alkyl, R16 and R12 are independently of one another identical or different and are
a) hydrogen atom,
b) —$(C_1-C_6)$-alkyl, wherein alkyl is unsubstituted or mono-, di- or trisubstituted independently of one another by R13,
c) —C(O)—$(C_1-C_4)$-alkyl,
d) —$(C_6-C_{14})$-aryl-, wherein aryl is unsubstituted or mono-, di- or trisubstituted independently of one another by R13,
e) —$(C_4-C_{14})$-heteroaryl, wherein heteroaryl is unsubstituted or mono-, di- or trisubstituted independently of one another by R13, R13 is halogen, —$NO_2$, —CN, =O, —OH, —$(C_1-C_8)$-alkyl, —$(C_1-C_8)$-alkoxy, —$CF_3$, phenyloxy-, —C(O)—R15, —C(O)—O—R17, —C(O)—N(R17)-R18, —N(R17)-R18, —N(R15)-$SO_2$—R15, —S—R15, —$SO_n$—R15, wherein n is 1 or 2, —$SO_2$—N(R17)-R18-, —$(C_6-C_{14})$-aryl, wherein aryl is unsubstituted or mono-, di- or trisubstituted independently of one another by R14, —(C$_4$-C$_{14}$)-heteroaryl, wherein heteroaryl is unsubstituted or mono-, di- or trisubstituted independently of one another by R14, —(C$_3$-C$_8$)-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, R14 is halogen, —OH, =O, —CN, —CF$_3$, —(C$_1$-C$_8$)-alkyl, —(C$_1$-C$_4$)-alkoxy, —NO$_2$, —C(O)—OH, —CN, —NH$_2$, —C(O)—O—(C$_1$-C$_4$)-alkyl, —(C$_1$-C$_8$)-alkylsulfonyl, —C(O)—NH—(C$_1$-C$_8$)-alkyl, —C(O)—N—[(C$_1$-C$_8$)-alkyl]$_2$, —C(O)—NH$_2$, —S—R15, —N(R15)-C(O)—NH—(C$_1$-C$_8$)-alkyl, or —N(R15)-C(O)—N—[(C$_1$-C$_8$)-alkyl]$_2$, R17 and R18 are independently of one another identical or different and are
  a) hydrogen atom,
  b) —(C$_1$-C$_6$)-alkyl,
  c) —(C$_6$-C$_{14}$)-aryl- or
  d) —(C$_4$-C$_{14}$)-heteroaryl,
said process comprises reacting a compound of formula II,

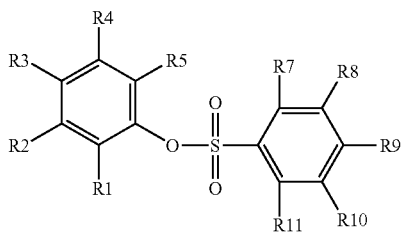

wherein R1, R2, R3, R4 and R5 are as defined in formula I and R7, R8, R9, R10 and R11 are
  a) hydrogen atom,
  b) —(C$_1$-C$_4$)-alkyl,
  c) halogen,
  d) —(C$_1$-C$_3$)-fluoroalkyl,
  e) —O—CF$_3$,
  f) —NO$_2$,
  g) —CN,
  h) —OH,
  i) —C(O)—R15,
  j) —C(O)—O—R16,
  k) —C(O)—N(R16)-R12,
  l) —N(R16)-R12,
  m) —SO$_n$—R15, wherein n is 1 or 2, or
  n) —SO$_2$—N(R16)-R12,
with a compound of formula III

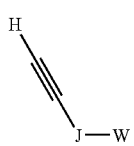

wherein J and W are as defined in formula I,
in the presence of a palladium catalyst, a base, a bidentate ligand and a protic solvent to give a compound of formula I and optionally the compound of formula I is converted to its physiologically tolerated salt.

2) The present invention also relates to a process for the preparation of compounds of formula I, wherein J is a covalent bond;
  —(C$_1$-C$_6$)-alkylene, wherein alkylene is unsubstituted or mono-, di- or trisubstituted independently of one another by R6;
  —(C$_3$-C$_6$)-cycloalkyl, wherein cycloalkyl is unsubstituted or mono-, di- or trisubstituted independently of one another by R14;
  phenyl, wherein phenyl is unsubstituted or mono-, di-, tri- or four times substituted independently of one another by R13; or
  —(C$_4$-C$_{14}$)-heteroaryl, wherein heteroaryl is selected from acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and is unsubstituted or mono-, di-, tri- or four times substituted independently of one another by R13;
W is hydrogen atom,
  —(C$_1$-C$_6$)-alkyl, wherein alkyl is unsubstituted or mono-, di- or trisubstituted independently of one another by R6;
  —(C$_3$-C$_6$)-cycloalkyl, wherein cycloalkyl is unsubstituted or mono-, di- or trisubstituted independently of one another by R6;

phenyl, wherein phenyl is unsubstituted or mono-, di-, tri- or four times substituted independently of one another by R6; or
—($C_4$-$C_{14}$)-heteroaryl, wherein heteroaryl is as defined above and is unsubstituted or mono-, di-, tri- or four times substituted independently of one another by R6;

R1, R2, R3, R4, R5 and R6 are independent of one another identical or different and are
  a) hydrogen atom,
  b) —($C_1$-$C_4$)-alkyl, wherein alkyl is unsubstituted or substituted one to three times by R13,
  c) halogen,
  d) phenyloxy-, wherein phenyloxy is unsubstituted or substituted one to three times by R13,
  e) —($C_1$-$C_3$)-fluoroalkyl,
  f) —N(R15)-($C_1$-$C_4$)-alkyl, wherein alkyl is unsubstituted or substituted one to three times by R13,
  g) phenyl, wherein phenyl is as defined above and is unsubstituted or mono-, di-, tri- or four times substituted independently of one another by R13,
  h) —($C_4$-$C_{14}$)-heteroaryl, wherein heteroaryl is as defined above and is unsubstituted or mono-, di-, tri- or four times substituted independently of one another by R13,
  i) —($C_3$-$C_8$)-cycloalkyl, wherein said cycloalkyl is unsubstituted or mono-, di-, tri- or four times substituted independently of one another by R13,
  j) a 3- to 7-membered cyclic residue is selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxathiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13,
  k) —O—$CF_3$,
  l) —O—($C_1$-$C_4$)-alkyl, wherein alkyl is unsubstituted or substituted one to three times by R13,
  m) —$NO_2$,
  n) —CN,
  o) —OH,
  p) —C(O)—R15,
  q) —C(O)—O—R16,
  r) —C(O)—N(R16)-R12,
  s) —N(R16)-R12,
  t) —N(R15)-$SO_2$—R15,
  v) —S—R15,
  w) —$SO_n$—R15, wherein n is 1 or 2,
  x) —$SO_2$—N(R16)-R12 or
  y) —Si(R16)(R16)-R12, or R1 and R2, R2 and R3, R3 and R4 or R4 and R5 form together with the atoms which they are attached to a phenyl ring, wherein phenyl is unsubstituted or substituted by R14, R15 is hydrogen atom, —($C_1$-$C_3$)-fluoroalkyl or —($C_1$-$C_6$)-alkyl, R16 and R12 are independently of one another identical or different and are
  a) hydrogen atom,
  b) —($C_1$-$C_4$)-alkyl, wherein alkyl is unsubstituted or mono-, di- or trisubstituted independently of one another by R13,
  c) —C(O)—($C_1$-$C_4$)-alkyl,
  d) phenyl, wherein phenyl is unsubstituted or mono-, di- or trisubstituted independently of one another by R13,
  e) —($C_4$-$C_{14}$)-heteroaryl, wherein heteroaryl is as defined above and is unsubstituted or mono-, di- or trisubstituted independently of one another by R13, R13 is F, Cl, —CN, =O, —OH, —($C_1$-$C_8$)-alkyl, —($C_1$-$C_8$)-alkoxy, —$CF_3$, phenyloxy-, —C(O)—R15, —C(O)—O—R17, —C(O)—N(R17)-R18, —N(R17)-R18, —$SO_2$—N(R17)-R18, —N(R15)-$SO_2$—R15, —S—R15, —$SO_n$—R15, wherein n is 1 or 2, phenyl, wherein phenyl is unsubstituted or mono-, di- or trisubstituted independently of one another by R14, —($C_4$-$C_{14}$)-heteroaryl, wherein heteroaryl is as defined above and is unsubstituted or mono-, di- or trisubstituted independently of one another by R14, —($C_3$-$C_6$)-cycloalkyl, wherein said cycloalkyl is unsubstituted or mono-, di- or trisubstituted independently of one another by R14, or a 3- to 7-membered cyclic residue, which is as defined above and is unsubstituted or mono-, di- or trisubstituted independently of one another by R14, R14 is F, Cl, —OH, =O, —CN, —$CF_3$, —($C_1$-$C_8$)-alkyl, —($C_1$-$C_4$)-alkoxy, —C(O)—OH, —CN, —$NH_2$, —C(O)—O—($C_1$-$C_4$)-alkyl, —($C_1$-$C_8$)-alkylsulfonyl, —C(O)—$NH_2$, —C(O)—NH—($C_1$-$C_8$)-alkyl, —C(O)—N—[($C_1$-$C_8$)-alkyl]$_2$, —S—R15, —N(R15)-C(O)—NH—($C_1$-$C_8$)-alkyl or —N(R15)-C(O)—N—[($C_1$-$C_8$)-alkyl]$_2$, R17 and R18 are independently of one another identical or different and are
  a) hydrogen atom,
  b) —($C_1$-$C_4$)-alkyl,
  c) phenyl or
  d) —($C_4$-$C_{14}$)-heteroaryl, wherein heteroaryl is as defined above, R7, R8, R9, R10 and R11 are
  a) hydrogen atom,
  b) —($C_1$-$C_4$)-alkyl,
  c) halogen,
  d) —($C_1$-$C_3$)-fluoroalkyl,
  e) —O—$CF_3$,
  f) —$NO_2$,
  g) —CN,
  h) —OH,
  i) —C(O)—R15,
  j) —C(O)—O—R16,
  k) —C(O)—N(R16)-R12,
  l) —N(R16)-R12,
  m) —$SO_n$—R15, wherein n is 1 or 2, or
  n) —$SO_2$—N(R16)-R12.

3) The invention also relates to a process for the preparation of a compound of formula I, wherein J is a covalent bond, —($C_1$-$C_6$)-alkylene, wherein alkylene is unsubstituted or mono- or disubstituted independently of one another by R6, cyclohexenyl, cyclohexyl, phenyl, wherein phenyl is unsubstituted or mono- or disubstituted independently of one another by R13 or thienyl, W is hydrogen atom, —($C_1$-$C_4$)-alkyl, wherein alkyl is unsubstituted or mono- or disubstituted independently of one another by R6, cyclohexenyl, cyclohexyl, phenyl, wherein phenyl is unsubstituted or mono- or disubstituted independently of one another by R6 or piperidinyl, R1, R2, R3, R4, R5 and R6 are independent of one another identical or different and are
 a) hydrogen atom,
 b) —($C_1$-$C_4$)-alkyl, wherein alkyl is unsubstituted or substituted one time by R13,
 c) fluorine,
 d) chlorine,
 e) —$CF_3$,
 f) —N(R15)-($C_1$-$C_4$)-alkyl,
 g) —O—$CF_3$,
 h) —O—($C_1$-$C_4$)-alkyl,
 i) —CN,
 j) —OH,
 k) —C(O)—R15,
 l) —C(O)—O—R16, or
 m) —N(R16)-R12, or R1 and R2, R2 and R3, R3 and R4 or R4 and R5 form together with the atoms which they are attached to a phenyl ring, wherein phenyl is unsubstituted or substituted by —CN, R15 is hydrogen atom or —($C_1$-$C_4$)-alkyl, R16 and R12 are independently of one another identical or different and are
 a) hydrogen atom,
 b) —($C_1$-$C_4$)-alkyl, or
 c) —C(O)—($C_1$-$C_4$)-alkyl, R13 is F, Cl, —CN or —N(R17)-R18, R14 is F, Cl or —CN, R17 and R18 are independently of one another identical or different and are hydrogen atom or —($C_1$-$C_4$)-alkyl, and R7, R8, R9, R10 and R11 are independently of one another identical or different and are hydrogen atom or methyl.

4) The invention also relates to a process for the preparation of a compound of formula I, which are N-(2-Hept-1ynyl-phenyl)-acetamide,
N-(2-Cyclohex-1-enylethynyl-phenyl)-acetamide,
N-(2-Thiophen-3-ylethynyl-phenyl)-acetamide,
N-(2-Phenylethynyl-phenyl)-acetamide,
N-[2-(4-Amino-phenylethynyl)-phenyl]-acetamide,
N-[2-(3-Diethylamino-prop-1-ynyl)-phenyl]-acetamide,
4-(3-Diethylamino-prop-1-ynyl)-3-methyl-benzoic acid ester,
3-Acetylamino-4-hept-1-ynyl-benzoic acid methyl ester,
1-(4-Hept-1-ynyl-3-methoxy-phenyl)ethanone,
1-(–3-Methoxy-4-(5-phenyl-pent-1-ynyl)-ethanone,
1-(4-Cyclohex-1-enylethynyl-3-methoxy-phenyl)ethanone,
1-[–4-(3,4-Dimethoxy-phenylethynyl)-3-methoxy-phenyl]-ethanone,
1-(5-Phenyl-pent-1-ynyl)-3-trifluoromethyl-benzene,
1-Cyclohexylethynyl-3-trifluoromethyl-benzene,
1-Cyclohex-1-enylethynyl-3-trifluoromethyl-benzene,
4-(5-Phenyl-pent-1-ynyl)-benzaldehyde,
4-Hept-1-ynyl-benzaldehyde,
4-Cyclohex-1-enylethynyl-benzaldehyde,
4-Hex-1-ynyl-benzonitrile,
4-(4-Pipreidin-1-yl-phenylethynyl)-benzonitrile,
4-(3-Diethylamino-prop-1-ynyl)-benzonitrile,
[(4-Hept-1-ynyl)-phenyl)]-acetonitrile,
[4-(5-Phenyl-pent-1-ynyl)-phenyl)]-acetonitrile,
1-Hept-1-ynyl-4-trifluoromethoxy-benzene,
2-(5-Phenyl-pent-1-ynyl)-4-trifluoromethoxy-benzene,
1-Cyclohex-1-enylethynyl-4-trifluoromethoxy-benzene,
1,2-Dimethoxy-4-(4-Trifluoromethoxy-phenylethynyl)-benzene,
4-(4-Trifluoromethoxy-phenylethynyl)-phenylamine,
1-Chloro-3-fluoro-5-hept-1-ynyl-benzene
1-Chloro-3-fluoro-5-phenylethynyl-benzene
1-Chloro-3-fluoro-5-hept-1-ynyl-benzene
1-Chloro-3-fluoro-5-phenylethynyl-benzene
4-(5-Cyano-pent-1-ynyl)-3-methoxy-benzonitrile
4-(3-Diethylamino-prop-1-ynyl)-3-methoxy-benzonitrile
6-(6-Hydroxy-hex-1-ynyl)-naphtalene-2-carbonitrile or
6-(4-Methoxy-phenylethynyl)-naphtalene-2-carbonitrile.

The protic solvent useful in the process of the present invention must be a solvent, wherein the compounds of formulae II and III, the palladium catalyst, the base and bidentate ligand are soluble or at least partially soluble and is compatible and chemically inert under the process conditions and does not contain oxygen as impurity.

Examples of said protic solvents are: water, methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol. Preferred is i-butanol, t-butanol, 2-methylbutan-2-ol, 3-methyl-3-pentanol, 3-ethyl-3-pentanol. Most preferred is t-butanol.

The base useful in this process of the present invention is a basic organic or inorganic compound and acts as proton acceptor without inhibiting the catalytic activity of the employed palladium. Suitable classes of such bases are for example carbonates, phosphates, fluorides, alkoxides and hydroxides with a suitable metal as counter ion. Carbonates and phosphates are the preferred bases in the process of the present invention. Potassium carbonate or caesium carbonate and in particular potassium phosphate are the preferred bases.

The bases are generally employed in moderate excess based on the aryl-1-tosylate of the compound of formula II. A useful range is a 1.5 to 4 fold excess based on the aryl-1-tosylate of the compound of formula II. The base may be favourably employed in a 3 fold excess based on the aryl-1-tosylate of the compound of formula II.

The palladium catalyst useful in this process can be selected from the following classes: Pd-alkanoates, Pd-alkanoate complexes, Pd-acetonates, Pd-halides, Pd-halide complexes, Pd-phosphine complexes. Representative examples include, but are not limited to, provided that the catalyst contains no monophosphino-biphenyl derivative as a ligand: palladium (II) acetate, palladium (II) trifluoroacetate, palladium (II) hexafluoroacetylacetonate, palladium (II) bromide, palladium (II) chloride, palladium (II) iodide, palladium (II) nitrate, palladium (II) acetylacetonate, dichloro-bis-acetonitrile palladium (II), tetrakis(triphenylphosphine) palladium (0), trans-di(μ-acetato)bis[o-(di-o-tolylphosphino)benzyl]dipalladium (II), tris(dibenzylideneacetone)dipalladium(0), tris(dibenzylideneacetone)dipalladium(0) chloroform adduct, palladium (II) chloride, 2,2'-bis(diphenylphosphino)-1,1'-binaphthylpalladium(II) chloride, acetato(2'-di-tert-butylphosphino-1,1'-biphenyl-2-yl)palladium(II), (1,2-Bis(diphenylphosphino)ethane)-dichloropalladium(II), Bis[1,2-bis(diphenylphosphino)ethane]palladium (0), [(2S,3S)-Bis(diphenylphosphino)butane][eta3-allyl]palladium(II) perchlorate, 1,3-bis(2,4,6-trimethylphenyl)imidazol-2-ylidene(1,4-naphthoquinone)palladium (0) dimer, [P,P'-1,3-bis(di-i-propylphosphino)propane][P-1,3-bis(di-i-propylphosphino)propane]palladium (0), 2-(dimethylamino)ferrocen-1-yl-palladium(II) chloride dinorbornylphosphine complex, chloro(di-2-norbornylphosphino)(2-dimethylaminomethylferrocen-1-yl)palladium (II), 1,1'-bis(diphenylphosphino)ferrocene palladium (II) chloride, dichloro[1, 1'-bis(diphenylphosphino)ferrocene]palladium (II) dichloromethane adduct, dichloro((S)—N,N-dimethyl-1-((R)-2-(diphenylphosphino)ferrocenyl)ethylamine)-palladium, (1,1'-bis(diphenylphosphino)ferrocene)palladium(II) chloride, [(2S)-1-[(1S)-1-[bis(1,1-dimethylethyl)phosphino-kappaP]ethyl]-2-(diphenylphosphino-kappaP)ferrocene] palladium dichloride, [(2S)-1-[(1S)-1-[bis(1,1-dimethylethyl)phosphino-kappaP]ethyl]-2-(diphenylphosphino-kappaP)ferrocene]-[tris(2-methylphenyl)phosphine] palladium, [(2R)-1-[(1R)-1-[bis(1,1-dimethylethyl)-phosphino-kappaP]ethyl]-2-(dicyclohexylphosphino-kappaP)ferrocene][tris(2-methylphenyl)phosphine] palladium. The preferred catalysts are palladium (II) acetate and in particular palladium (II) trifluoroacetate.

The palladium catalyst is generally employed in an amount in the range of 0.1 to 30 mole percent based on the aryl-1-tosylate of the compound of formula II. A useful range is 1 to 9 mole percent of palladium catalyst based on the aryl-1-tosylate of the compound of formula II.

The ligand useful in this process is a bidentate phosphine ligand and can be selected from the following compounds, but are not limited to: (+/−)-2,2'-bis(diphenylphosphino)-1,1'-binaphthalene, (9,9-dimethyl-9h-xanthene-4,5-diyl)bis[diphenyl phosphine], (R)-(−)-1-[(S)-2-(diphenylphosphino) ferrocenyl]ethyldicyclohexylphosphine, 1,2-Bis(diphenylphosphino)ethane, (2S,3S)-(−)-bis(diphenylphosphino) butane, 1,3-Bis(diphenylphosphino)propane, (R)-(−)-1-[(S)-2-(Dicyclohexylphosphino)ferrocenyl]-ethyldi-tert-butylphosphine, (R)-(+)-1,1'-Bis(diphenylphosphino)-2,2'-bis(N,N-diisopropylamido)ferrocene, (S,S)-1-[1-(Di-tert-butylphosphino)ethyl]-2-(diphenylphosphino)ferrocene, (1R,2R)-(+)-1,2-Diaminocyclohexane-N,N'-bis(2-diphenylphosphino-1-naphtoyl, (−)-1,2-Bis((2S,5S)-2,5-diisopropylphospholano)-benzene, Bis[(2-diphenylphosphino) phenyl]ether, (S)-(−)-2,2'-Bis(di-para-tolylphosphino)-1,1'-binaphyl, 4,5-Bis(bis(3,5-bis(trifluoromethyl)phenyl)-phosphino)-9,9-dimethylxanthen, (R)-(−)-1-[(S)-2-(di(3,5-bis-trifluoromethylphenyl)-phosphino)ferrocenyl] ethyldicyclohexylphosphine, (R)-(−)-1-[(S)-2-(di(3,5-bis-trifluoromethylphenyl)phosphino)ferrocenyl]ethyldi(3,5-dimethylphenyl)phosphine, 2,2'-bis[(2',4',6'-triisopropyl) dicyclohexylphosphino]-biphenyl, 2,2'-bis(di-tert-butylphosphino)biphenyl, (R)-(+)-1-[(R)-2-(2"-di(3,5-xylyl) phosphinophenyl)-ferrocenyl]ethyldi(3,5-xylyl)phosphine, (R)-(−)-1-[(S)-2-(bis(3,5-dimethyl-4-methoxyphenyl)phosphino)ferrocenyl]ethyldicyclohexylphosphine, (R)-(+)-1-[(R)-2-(2"-di(3,5-dimethyl-4-methoxyphenyl)phosphinophenyl)ferrocenyl]ethyldi(bis-3,5-trifluoromethylphenyl) phosphine, (R)-(−)-1-[(S)-2-(dicyclohexylphosphino)-ferrocenyl]ethyldi-t-butylphosphine, (R)-(+)-1-[(S)-2-bis(4-trifluoromethylphenyl)-phosphino)ferrocenyl]ethyl-di-t-butylphosphine, (1,1'-ferrocenediyl)-phenylphosphine, (R)-(+)-1,1'-bis(diphenylphosphino)-2,2'-bis(N,N-diisopropylamido)ferrocene, 1,2,3,4,5-pentaphenyl-1'-(di-t-butylphosphino)-ferrocene, (S)-(+)-1-[(R)-2-(diphenylphosphino)ferrocenyl]ethyldi-t-butylphosphine, (R)-(−)-1-[(S)-2-(diphenylphosphino) ferrocenyl]ethyldi-t-butylphosphine, (S)-(+)-1-[(R)-2-(dicyclohexylphosphino)ferrocenyl]ethyldiphenylphosphine, 1,1'-bis(di-i-propylphosphino)ferrocene, (R)-(−)-1-[(S)-2-(dicyclohexylphosphino)-ferrocenyl]ethyldiphenylphosphine, (S)-(+)-1-[(R)-2-(dicyclohexylphosphino) ferrocenyl]ethyldicyclohexylphosphine, (R)-(−)-1-[(S)-2-(dicyclohexylphosphino) ferrocenyl]ethyldicyclohexylphosphine, (R)-(−)-1-[(S)-2-(diphenylphosphino) ferrocenyl]ethyldicyclohexylphosphine, 1,1'-bis(di-tert-butylphosphino) ferrocene, (−)-(R)-1-((S)-2-(diphenylphosphino)ferrocenyl) ethyl methyl ether, (+)-(S)-1-((R)-2-(diphenylphosphino) ferrocenyl)ethyl methyl ether, (+)-(S)—N,N-dimethyl-1-((R)-1',2-bis(diphenylphosphino)ferrocenyl)ethylamine, (+)-(S)—N,N-dimethyl-1-((R)-2-(diphenylphosphino)ferrocenyl)ethylamine, 1,1'-bis(diphenylphosphino)ferrocene. Most favourably bidentate ligands like 1-[2-(dicyclohexylphosphino)ferrocenyl]ethyldi-t-butylphosphine, 1-[2-(diphenylphosphino)ferrocenyl]ethyldi-t-butylphosphine are employed in particular in combination with a palladium source bearing no phosphine itself, like e.g. dichloro-bis-acetonitrile palladium (II), palladium (II) bromide, palladium (II) iodide, palladium (II) acetate, palladium (II) trifluoroacetate, tris(dibenzylideneacetone)dipalladium(0), palladium (II) chloride. The most preferred bidentate ligand is 1-[2-(dicyclohexylphosphino) ferrocenyl]ethyldi-t-butylphosphine.

The phosphine ligand is generally employed in an amount in the range of 0.1 to 60 mole percent based on the aryl-1-tosylate of the compound of formula II. A useful range is from 1 to 10 mole percent of phosphine ligand based on the aryl-1-tosylate of the compound of formula II. Most favourably the phosphine ligand is employed in a range from 1.5 to 3, in particular a 2.3 ratio with respect to the palladium source.

The process is carried out in the temperature range 60° C. to 150° C. A useful temperature is about 70° C. to 100° C. Generally the process is carried out under the exclusion of air like e.g. in an argon or nitrogen atmosphere at atmospheric pressure. The process time is in the range of 3 to 48 hours (h).

The progress of each process may be monitored by methods known to those skilled in the art, like for example thin layer silica gel chromatography, gas chromatography, nuclear magnetic resonance, infrared spectroscopy, and high pressure liquid chromatography combined with ultraviolet detection or mass spectroscopy. Preferably thin layer silica gel chromatography and high pressure liquid chromatography (HPLC) combined with mass spectroscopy are used.

The isolation and purification procedures useful for the compounds obtained by the process of the present invention are well-known to those skilled in the art, like for example filtration through a celite containing cartridge, aqueous workup, extraction with organic solvents, distillation, crystallisation, chromatography on silica, and high pressure liquid chromatography (HPLC) on normal phase or reversed phase. Preferred methods include, but are not limited to those exemplified.

The term alkyl as used herein expressly includes saturated groups as well as unsaturated groups which latter groups contain one or more, for example one, two or three, double bonds and/or triple bonds. All these statements also apply if an alkyl group occurs as a substituent on another residue, for example in an alkyloxy residue, an alkyloxycarbonyl residue or an arylalkyl residue. Examples of "—($C_1$-$C_8$)-alkyl" or "—($C_1$-$C_8$)-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. Unsaturated alkyl residues are e.g. alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3- pentadienyl, or alkynyl residues such as ethynyl, 1-propynyl, 2-propynyl (=propargyl) or 2-butynyl. Alkyl residues can also be unsaturated when they are substituted.

The term "—($C_3$-$C_8$)-cycloalkyl" is understood as cyclic alkyl residues are cycloalkyl residues containing 3, 4, 5, 6, 7 or 8 ring carbon atoms like cyclopropyl, cyclobutyl, cyclopentyl, cyclohexyl, cyloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom. The term "—($C_6$-$C_{14}$)-aryl" is understood as meaning aromatic hydrocarbon radicals containing from 6 to 14 carbon atoms in the ring. Examples of —($C_6$-$C_{14}$)-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals. The term "—($C_4$-$C_{14}$)-heteroaryl" refers to mono-, di- or tri-ring systems, wherein one or more of the 4 to 14 ring carbon atoms are replaced by heteroatoms such as nitrogen, oxygen or sulfur. Examples are acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benztriazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "a 3- to 7-membered cyclic residue, containing 1, 2, 3 or 4 heteroatoms" refer to structures of heterocycles, which can be derived from compounds such as azepine, azetidine, aziridine, azirine, 1,4 diazepane, 1,2-diazepine, 1,3-diazepine, 1,4-diazepine, diazirine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The 3- to 7-membered monocyclic group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl.

The term "R1 and R2, R2 and R3, R3 and R4 or R4 and R5 form together with the atoms which they are attached to a 5- or 8-membered ring, containing up to 0, 1, 2, 3 or 4 heteroatoms chosen from nitrogen, sulfur or oxygen" refers to residues which can be derived from compounds such as azepine, azirine, azocane, azocane-2-one, cyloheptyl, cyclohexyl, cyclooctane, cyclooctene, 1,4-diazepane, 1,2-diazepine, 1,3-diazepine, 1,4-diazepine, [1,2]diazocan-3-one, [1,3]diazocan-2-one, [1,4]diazocane, dioxazine, dioxazole, [1,4]dioxocane, 1,3-dioxolane, dioxole, 1,3-dioxolene, furan, imidazole, imidazolidine, imidazoline, isothiazole, isothiazolidine, isothiazoline, isothiazole, isoxazole, isoxazolidine, isoxazoline, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxaziridine, [1,4]oxazocane, [1,3]oxazocan-2-one, oxocane, oxocan-2-one, oxazole, piperidine, piperazine, phenyl, pyridazine, pyridine, pyrimidine, pyran, pyrazine, pyrazole, pyrazolepyrrole, pyrazolidine, pyrazoline, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, tetrazole, thiadiazine, thiadiazole, 1,2-thiazine, 1,3-thiazine, 1,4-thiazine, thiazole, 1,3-thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole. The fact that many of the before-listed names of heterocycles are the chemical names of unsaturated or aromatic ring systems does not imply that the, 4- to 14-membered mono- or polycyclic group could only be derived from the respective unsaturated ring system. The names here only serve to describe the ring system with respect to ring size and the number of the heteroatoms and their relative positions. As explained above, the 4- to 14-membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline or 1,2,3,4-tetrahydroisoquinoline.

The term "—$(C_1$-$C_3)$-fluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

Halogen is fluorine, chlorine, bromine or iodine, preferably fluorine, chlorine or bromine, particularly preferably chlorine or bromine.

The term "tosylate" or "Tos" refers to p-toluenesulfonic acid ester or p-toluenesulfonate.

The term "triflate" or "Tf" refers to trifluoro-methanesulfonic acid ester or trifluoromethanesulfonate.

The term "nonaflate" refers to 1,1,2,2,3,3,4,4,4-nonafluoro-1-butanesulfonic acid ester or 1,1,2,2,3,3,4,4,4-nonafluoro-1-butanesulfonate.

Optically active carbon atoms present in the compounds of the formula (I) can independently of each other have R configuration or S configuration. The compounds of the formula (I) can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula (I), and it comprises all ratios of the stereoisomers in the mixtures. In case the compounds of the formula (I) can be present as E isomers or Z isomers (or cis isomers or trans isomers) the invention relates both to pure E isomers and pure Z isomers and to E/Z mixtures in all ratios. The invention also comprises all tautomeric forms of the compounds of the formula (I).

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula (I) can also be obtained by employing stereochemically uniform starting materials or by using stereoselective reaction conditions.

The starting materials or building blocks for use in the general synthetic procedures that can be applied in the preparation of the compounds of formula (I) are readily available to one of ordinary skill in the art. In many cases they are commercially available or have been described in the literature. Otherwise they can be prepared from readily available precursor compounds analogously to procedures described in the literature, or by procedures or analogously to procedures described in this application.

Further, in order to obtain the desired substituents in the aryl nucleus of the ring system in the formula (I), the functional groups introduced into the ring system during the cross-coupling process can be chemically modified. For example, an aryl ring carrying a hydrogen atom at the 2-position can also be obtained by oxidation of 2-methyl aryl-1-alkyne to the aryl-1-alkyne-2-carboxylic acid and subsequent decarboxylation or from aryl-1-alkynes carrying an ester group in the respective position. Carboxylic acid groups and acetic acid groups in for example the 2-position can be converted into their homologues by usual reactions for chain elongation of carboxylic acids.

Especially the groups present in aryl ring system can be modified by a variety of processes and thus the desired residues R1, R2, R3, R4, R5 and R6 be obtained. For example, nitro groups can be reduced to amino group with under the described process conditions or by various reducing agents, such as sulfides, dithionites, complex hydrides or by catalytic hydrogenation. A reduction of a nitro group may also be carried out at a later stage of the synthesis of a compound of the formula (I), and a reduction of a nitro group to an amino group may also occur simultaneously with the process performed on another functional group, for example when reacting a group like a cyano group with hydrogen sulfide or when hydrogenating a group. Ester groups present in the aryl nucleus can be hydrolyzed to the corresponding carboxylic acids, which after activation can then be reacted with amines or alcohols under standard conditions. Ether groups present at the benzene nucleus, for example benzyloxy groups or other easily cleavable ether groups, can be cleaved to give hydroxyl groups which then can be reacted with a variety of agents, for example etherification agents or activating agents allowing replacement of the hydroxyl group by other groups. Sulfur-containing groups can be reacted analogously.

Due to the fact that in the present case the functional groups are attached to an aryl ring it may in certain cases become necessary to specifically adapt process conditions or to choose specific reagents from a variety of reagents that can in principle be employed into a conversion process, or otherwise to take specific measures for achieving a desired conversion, for example to use protection group techniques. However, finding out suitable process variants and process conditions in such cases does not cause any problems for one skilled in the art.

In the course of the preparation of the compounds of the formula I it can generally be advantageous or necessary to introduce functional groups which reduce or prevent undesired processes or side reactions in the respective synthesis step, in the form of precursor groups which are later converted into the desired functional groups, or to temporarily block functional groups by a protective group strategy suited to the synthesis problem. Such strategies are well known to those skilled in the art. As example of a precursor group cyano groups may be mentioned, which can in a later reaction step be transformed into carboxylic acid derivatives or reduced to an aminomethyl group. Protective groups can also have the meaning of a solid phase, and cleavage from the solid phase stands for the removal of the protective group. The use of such techniques is known to those skilled in the art. For example, a phenolic hydroxy group can be attached to a trityl-polystyrene resin, which serves as a protecting group, and the molecule is cleaved from this resin by treatment with trifluoroacetate at a later stage of the synthesis.

In the course of the synthesis the employment of microwave assistance for speeding-up, facilitating or enabling reactions may be beneficial or even required in many cases. Some processes are for example described by J. L. Krstenansky, I. Cotteril, Curr. Opin. Drug. Disc. & Development., 4 (2000), 454.

Physiologically tolerable salts of the compounds of formula I are nontoxic salts that are physiologically acceptable, in particular, pharmaceutically utilizable salts. Such salts of compounds of formula I containing acidic groups, for example, a carboxyl group (COOH), include, for example, alkali metal salts or alkaline earth metal salts, such as sodium salts, potassium salts, magnesium salts and calcium salts, as well as salts with physiologically tolerable quaternary ammonium ions, such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of formula I, for example, amino groups or guanidino groups, form acid addition salts, for example, with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, for example, a guanidino group and a carboxyl group, can also be present as zwitterions (betaines) which are likewise included in the scope of the present invention.

Salts of compounds of formula I can be obtained by customary methods known to those skilled in the art, for example, by combining a compound of the formula I with an inorganic or organic acid or base in a solvent or dispersant, or from other salts by cation exchange or anion exchange. The present invention also includes all salts of the compounds of formula I which, because of low physiologically tolerability, are not directly suitable for use in pharmaceuticals but are suitable, for example, as intermediates for carrying out further chemical modifications of the compounds of formula I or as starting materials for the preparation of physiologically tolerable salts.

A further aspect of the invention is the use of a compound of the formula I as prepared by the process according to the invention for the production of pharmaceuticals, diagnostic agents, liquid crystals, polymers, herbicides, fungicidals, nematicidals, parasiticides, insecticides, acaricides and arthropodicides.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequence for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

EXAMPLES

Abbreviations

Argon Ar tert-Butyl tBu dibenzylidenacetone dba dichloromethane DCM

N,N-dimethyl-4-aminopyridine DMAP 1,1'-Bis(diphenylphosphino)ferrocene DPPF ethylacetate EtOAc Fast atom bombardment FAB High pressure liquid chromatography HPLC Liquid chromatography with mass spectrometry LC-MS Room temperature 21° C. to 24° C. RT Thin layer chromatography TLC 1-[2-(dicyclohexylphosphino)ferrocenyl]ethyldi-t-butylphosphine Cy-PF-t-Bu.

General Procedure for the Sonogashira Cross-Coupling Process:

Under an Ar atmosphere, a dry reaction tube was charged with the aryl tosylate of the formula II (0.5 mmol), palladium trifluoroacetate (5 mg, 0.015 mmol), Cy-PF-t-Bu (19.4 mg, 0.035 mmol) and $K_3PO_4$ (318 mg, 1.50 mmol). 2 mL of t-BuOH were then added followed by the addition of 1-alkyne of the formula III (1 mmol) [for the examples 29-32, 0.55 mmol was used]. The addition of the alkyne of the formula III was performed all at once and without delay. The tube was again purged with Ar, sealed and the reaction mixture was heated at 85° C. until the starting material had been consumed (TLC and LCMS). The reaction mixture was cooled to RT, diluted with EtOAc and filtered through a pad of Celite®. The filtrate was concentrated under reduced pressure and the residue was purified by flash chromatography on silica gel. The fractions containing the product were combined and the solvents were evaporated under reduced pressure to yield the desired aryl-alkyne product of formula I.

General Procedure for the Preparation of Aryl-Tosylates and Aryl Benzene-Sulfonic Acid Esters:

To a solution of the desired aryl alcohol (13.23 mmol) in DCM (150 mL) were added, under stirring, $Et_3N$ (17.20 mmol), DMAP (0.4 mmol) and p-toluenesulfonyl chloride (14.55 mmol) (or benzenesulfonyl chloride) successively. The resulting solution was stirred at RT until the starting material had been consumed (TLC and LCMS). The reaction mixture was then poured into a 1N HCl solution (100 mL) and extracted with DCM. The combined organic layers were washed with a saturated solution of $NaHCO_3$, brine and then dried over $Na_2SO_4$. The filtrate was concentrated under reduced pressure. When necessary, the residue obtained was purified by flash chromatography yielding the sulfonated compound of formula II.

Example 1

N-(2-Hept-1ynyl-phenyl)-acetamide

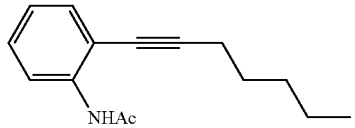 [SMILES: CCCCCC#Cc1ccccc1NC(C)=O]

This product was prepared from toluene-4-sulfonic acid 2-acetylamino-phenyl ester and 1-heptyne following the general procedure for the Sonogashira cross-coupling process described above. Chromatography eluent: heptane/EtOAc 8:2; yield (92 mg, 80%); $^1$H NMR δ (CDCl$_3$): 8.47 (d, J=8.51 Hz, 1H), 7.93 (br s, 1H), 7.36 (dm, 1H), 7.31-7.23 (m, 1H), 7.02 (t, J=7.22 Hz, 1H), 2.53 (t, J=7.08 Hz, 2H), 2.21 (s, 3H), 1.63 (p, J=7.11 Hz, 2H), 1.48-1.3 (m, 4H), 0.92 (t, J=7.2 Hz, 3H); LCMS m/z: 229.

Example 2

N-(2-Cyclohex-1-enylethynyl-phenyl)acetamide

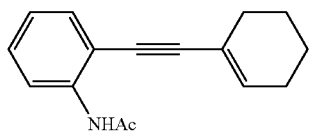 [SMILES: CC(=O)Nc1ccccc1C#CC1=CCCCC1]

This product was prepared from toluene-4-sulfonic acid 2-acetylamino-phenyl ester and 1-ethynyl-cyclohexene following the general procedure for the Sonogashira cross-coupling process described above. Chromatography eluent: heptane/EtOAc 9:1; yield (115 mg, 96%); $^1$H NMR δ (CDCl$_3$): 8.39 (d, J=8.53 Hz, 1H), 7.9 (br s, 1H), 7.37 (dm, 1H), 7.31-7.23 (m, 1H), 7.02 (t, J=7.22 Hz, 1H), 6.25 (m, 1H), 2.32-2.12 (m, 7H), 1.76-1.6 (m, 4H); LCMS m/z: 239.

Example 3

N-(2-Thiophen-3-ylethynyl-phenyl)-acetamide

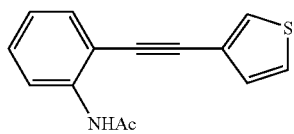

This product was prepared from toluene-4-sulfonic acid 2-acetylamino-phenyl ester and 3-ethynyl-thiophene following the general procedure for the Sonogashira cross-coupling process described above. Chromatography eluent: heptane/EtOAc 9:1; yield (48 mg, 40%); $^1$H NMR δ (CDCl$_3$): 8.39 (d, J=8.51 Hz, 1H), 7.9 (br s, 1H), 7.36-7.30 (m, 2H), 7.30-7.21 (m, 3H), 7.02 (t, J=7.24 Hz, 1H), 2.21 (s, 3H); LCMS m/z: 241.

Example 4

N-(2-Phenylethynyl-phenyl)-acetamide

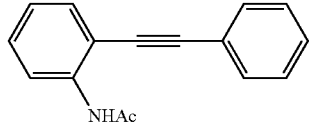 [SMILES: CC(=O)Nc1ccccc1C#Cc1ccccc1]

This product was prepared from toluene-4-sulfonic acid 2-acetylamino-phenyl ester and ethynyl-benzene following the general procedure for the Sonogashira cross-coupling process described above. Chromatography eluent: heptane/EtOAc 9:1; yield (60 mg, 50%); $^1$H NMR δ (CDCl$_3$): 8.39 (d, J=8.55 Hz, 1H), 7.9 (br s, 1H), 7.59-7.67 (m, 2H), 7.58-7.52 (m, 2H), 7.41-7.35 (m, 3H), 7.02 (t, J=7.22 Hz, 1H), 2.21 (s, 3H); LCMS m/z: 235.

Example 5

N-[2-(4-Amino-phenylethynyl)-phenyl]-acetamide

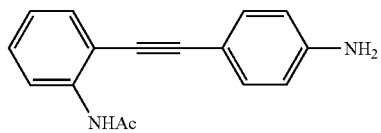 [SMILES: CC(=O)Nc1ccccc1C#Cc1ccc(N)cc1]

This product was prepared from toluene-4-sulfonic acid 2-acetylamino-phenyl ester and 4-ethynyl-phenylamine following the general procedure for the Sonogashira cross-coupling process described above. Chromatography eluent: heptane/EtOAc 9:1; yield (47 mg, 50%); $^1$H NMR δ (CDCl$_3$): 8.39 (d, J=8.52 Hz, 1H), 7.9 (br s, 1H), 7.59-7.67 (m, 2H), 7.58-7.52 (m, 2H), 7.41-7.35 (m, 2H), 7.02 (t, J=7.21 Hz, 1H), 3.82 (b, 2H), 2.21 (s, 3H); LCMS m/z: 250.

Example 6

N-[2-(3-Diethylamino-prop-1-ynyl)-phenyl]-acetamide

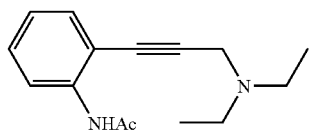 [SMILES: CCN(CC)CC#Cc1ccccc1NC(C)=O]

This product was prepared from toluene-4-sulfonic acid 2-acetylamino-phenyl ester and diethyl-prop-2-ynyl-amine following the general procedure for the Sonogashira cross-coupling process described above. Chromatography eluent: heptane/EtOAc 8:2; yield (73 mg, 60%); $^1$H NMR δ (CDCl$_3$): 8.47 (d, J=8.52 Hz, 1H), 7.93 (br s, 1H), 7.36 (dm, 1H), 7.31-7.23 (m, 1H), 7.02 (t, J=7.24 Hz, 1H), 3.54 (s, 2H), 2.62 (q, J=7.13 Hz, 4H), 2.21 (s, 3H), 1.11 (t, J=7.11 Hz, 6H); LCMS m/z: 244.

Example 7

4-(3-Diethylamino-prop-1-ynyl)-3-methyl-benzoic acid ester

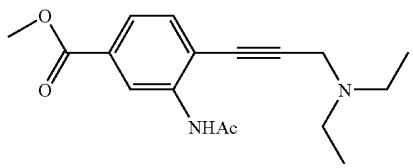 [SMILES: CCN(CC)CC#Cc1ccc(C(=O)OC)cc1NC(C)=O]

This product was prepared from 3-acetylamino-4-(toluene-4-sulfonyloxy)-benzoic acid methyl ester and diethyl-prop-2-ynyl-amine following the general procedure for the Sonogashira cross-coupling process described above. Chromatography eluent: heptane/EtOAc 8:2; yield (85 mg, 56%); $^1$H NMR δ (CDCl$_3$): 8.96 (d, J=1.52 Hz, 1H), 7.92 (br s, 1H), 7.66 (dd, J=1.51 Hz, 1H), 7.38 (d, J=8.10 Hz, 1H), 3.89 (s, 3H), 3.54 (s, 2H), 2.62 (q, J=7.12 Hz, 4H), 2.21 (s, 3H), 1.11 (t, J=7.11 Hz, 6H); LCMS m/z: 302.

Example 8

3-Acetylamino-4-hept-1-ynyl-benzoic acid methyl ester

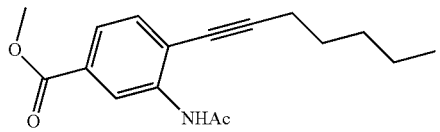 [SMILES: CCCCCC#Cc1ccc(C(=O)OC)cc1NC(C)=O]

This product was prepared from 3-acetylamino-4-(toluene-4-sulfonyloxy)-benzoic acid methyl ester and 1-heptyne following the general procedure for the Sonogashira cross-coupling process described above. Chromatography eluent: heptane/EtOAc 8:2; yield (80 mg, 55%); $^1$H NMR δ (CDCl$_3$): 8.96 (d, J=1.51 Hz, 1H), 7.92 (br s, 1H), 7.66 (dd, J=1.57, J=8.33 Hz, 1H), 7.38 (d, J=8.15 Hz, 1H), 3.89 (s, 3H), 2.53 (t, J=7.09 Hz, 2H), 2.21 (s, 3H), 1.63 (p, J=7.16 Hz, 2H), 1.48-1.3 (m, 4H), 0.92 (t, J=7.26 Hz, 3H); LCMS m/z: 287.

Example 9

1-(4-Hept-1-ynyl-3-methoxy-phenyl)ethanone

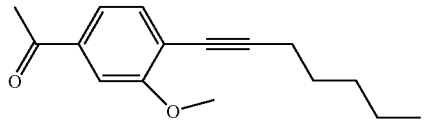 [SMILES: CCCCCC#Cc1ccc(C(C)=O)cc1OC]

This product was prepared from toluene-4-sulfonic acid 4-acetyl-2-methoxy-phenyl ester and 1-heptyne following the general procedure for the Sonogashira cross-coupling process described above. Chromatography eluent: heptane/DCM 1:1; yield (110 mg, 90%); $^1$H NMR δ (CDCl$_3$): 7.50-7.41 (m, 3H), 3.91 (s, 3H), 2.59 (s, 3H), 2.47 (t, J=7.14 Hz, 2H), 1.63 (p, J=7.22 Hz, 2H), 1.5-1.29 (m, 4H), 0.91 (t, J=7.13 Hz, 3H); LCMS m/z: 244.

Example 10

1-(-3-Methoxy-4-(5-phenyl-pent-1-ynyl)-ethanone

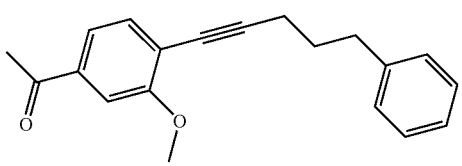 [SMILES: COc1cc(C(C)=O)ccc1C#CCCCc1ccccc1]

This product was prepared from toluene-4-sulfonic acid 4-acetyl-2-methoxy-phenyl ester and pent-4-ynyl-benzene following the general procedure for the Sonogashira cross-coupling process described above. Chromatography eluent: heptane/DCM 1:1; yield (94 mg, 64%); $^1$H NMR δ (CDCl$_3$): 7.5-7.41 (m, 3H), 7.44-7.18 (m, 5H), 3.92 (s, 3H), 2.81 (t, J=7.33 Hz, 2H), 2.51 (s, 3H), 2.5 (t, J=7.25 Hz, 2H), 1.95 (p, J=7.17 Hz, 2H); LCMS m/z: 292.

Example 11

1-(4-Cyclohex-1-enylethynyl-3-methoxy-phenyl)ethanone

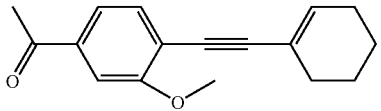

This product was prepared from toluene-4-sulfonic acid 4-acetyl-2-methoxy-phenyl ester and 1-ethynyl-cyclohexene following the general procedure for the Sonogashira cross-coupling process described above. Chromatography eluent: DCM; yield (114 mg, 90%); $^1$H NMR δ (CDCl$_3$): 7.53-7.41 (m, 3H), 6.29 (m, 1H), 3.92 (s, 3H), 2.51 (s, 3H), 2.31-2.12 (dm, 4H), 1.73-1.57 (m, 4H); LCMS m/z: 254.

Example 12

1-[-4-(3,4-Dimethoxy-phenylethynyl)-3-methoxy-phenyl]-ethanone

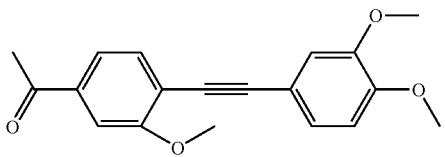 [SMILES: COc1cc(C(C)=O)ccc1C#Cc1ccc(OC)c(OC)c1]

This product was prepared from toluene-4-sulfonic acid 4-acetyl-2-methoxy-phenyl ester and 4-ethynyl-1,2-dimethoxy-benzene following the general procedure for the Sonogashira cross-coupling process described above. Chromatography eluent: DCM; yield (120 mg, 77%); $^1$H NMR δ (CDCl$_3$): 7.55 (d, J=8.26 Hz, 1H), 7.53-7.48 (m, 2H), 7.18

(dd, J=8.25 Hz, J=2.30 Hz, 1H), 7.07 (m, 1H), 6.84 (d, J=8.24 Hz, 1H), 3.98 (s, 3H), 3.91 (s, 6H), 2.61 (s, 3H); LCMS m/z: 310.

Example 13

1-(5-Phenyl-pent-1-ynyl)-3-trifluoromethyl-benzene

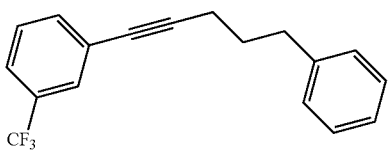

This product was prepared from toluene-4-sulfonic acid 3-trifluoromethyl-phenyl ester and pent-4-ynyl-benzene following the general procedure for the Sonogashira cross-coupling process described above. Chromatography eluent: heptane; yield (140 mg, 97%); $^1$H NMR δ (CDCl$_3$): 7.66 (s, 1H), 7.61-7.7.49 (m, 2H), 7.46-7.36 (m, 1H), 7.35-7.16 (m, 5H), 2.79 (t, J=7.15 Hz, 2H), 2.43 (t, J=7.20 Hz, 2H), 1.93 (p, J=7.11 Hz, 2H); LCMS m/z: 288.

Example 14

1-Cyclohexylethynyl-3-trifluoromethyl-benzene

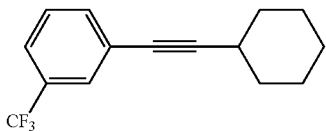 [SMILES: FC(F)(F)c1cccc(C#CC2CCCCC2)c1]

This product was prepared from toluene-4-sulfonic acid 3-trifluoromethyl-phenyl ester and ethynyl-cyclohexane following the general procedure for the Sonogashira cross-coupling process described above. Chromatography eluent: heptane; yield (82 mg, 65%); δ$_H$ (CDCl$_3$): 7.67 (s, 1H), 7.61-7.7.49 (m, 2H), 7.46-7.37 (m, 1H), 2.70-2.52 (m, 1H), 2.04-1.30 (m, 10H); LCMS m/z: 252.

Example 15

1-Cyclohex-1-enylethynyl-3-trifluoromethyl-benzene

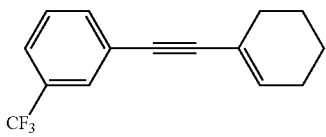 [SMILES: FC(F)(F)c1cccc(C#CC2=CCCCC2)c1]

This product was prepared from toluene-4-sulfonic acid 3-trifluoromethyl-phenyl ester and 1-ethynyl-cyclohexene following the general procedure for the Sonogashira cross-coupling process described above. Chromatography eluent: heptane; yield (106 mg, 85%); $^1$H NMR δ (CDCl$_3$): 7.68 (s, 1H), 7.6-7.7.49 (m, 2H), 7.46-7.37 (m, 1H), 6.28 (m, 1H), 2.31-2.12 (m, 4H), 1.73-1.57 (m, 4H); LCMS m/z: 250.

Example 16

4-(5-Phenyl-pent-1-ynyl)-benzaldehyde

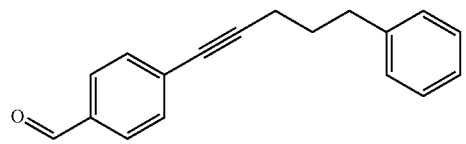 [SMILES: O=Cc1ccc(C#CCCCc2ccccc2)cc1]

This product was prepared from toluene-4-sulfonic acid 4-formyl-phenyl ester and pent-4-ynyl-benzene following the general procedure for the Sonogashira cross-coupling process described above. Chromatography eluent: heptane/DCM 1:1; yield (100 mg, 58%); $^1$H NMR δ (CDCl$_3$): 9.98 (s, 1H), 8.02 (d, J=8.61 Hz, 2H), 7.81 (d, J=8.63 Hz, 2H), 7.57-7.47 (m, 4H), 2.79 (t, J=7.18 Hz, 2H), 2.48 (t, J=7.17 Hz, 2H), 1.93 (p, J=7.23 Hz, 2H); LCMS m/z: 248.

Example 17

4-Hept-1-ynyl-benzaldehyde

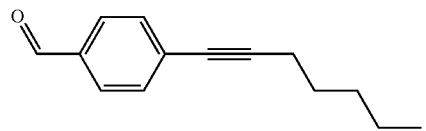

This product was prepared from toluene-4-sulfonic acid 4-formyl-phenyl ester and 1-heptyne following the general procedure for the Sonogashira cross-coupling process described above. Chromatography eluent: heptane/EtOAc 9:1; yield (60 mg, 70%); $^1$H NMR δ (CDCl$_3$): 10.02 (s, 1H), 7.8 (d, J=8.65 Hz, 2H), 7.53 (d, J=8.62 Hz, 2H), 2.45 (t, J=7.22 Hz, 2H), 1.62 (p, J=7.11 Hz, 2H), 1.48-1.3 (m, 4H), 0.93 (t, J=7.20 Hz, 3H); LCMS m/z: 200

Example 18

4-Cyclohex-1-enylethynyl-benzaldehyde

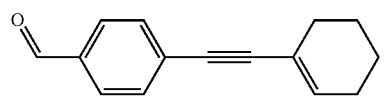

This product was prepared from toluene-4-sulfonic acid 4-formyl-phenyl ester and 1-ethynyl-cyclohexene following the general procedure for the Sonogashira cross-coupling process described above. Chromatography eluent: heptane/DCM 1:1; yield (71 mg, 68%); $^1$H NMR δ (CDCl$_3$): 9.99 (s, 1H), 8.02 (d, J=8.51 Hz, 2H), 7.52 (d, J=8.60 Hz, 2H), 6.31-6.27 (m, 1H), 2.14-2.22 (m, 4H), 1.58-1.73 (m, 4H); LCMS m/z: 210.

Example 19

4-Hex-1-ynyl-benzonitrile

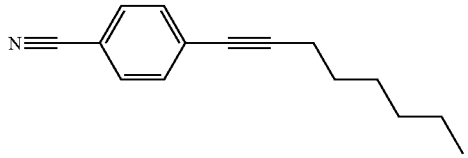 [SMILES: CCCCCCC#Cc1ccc(C#N)cc1]

This product was prepared from toluene-4-sulfonic acid 4-cyano-phenyl ester and 1-octyne following the general procedure for the Sonogashira cross-coupling process described above. Chromatography eluent: heptane/EtOAc 9:1; yield (100 mg, 95%); $^1$H NMR δ (CDCl$_3$): 7.56 (d, J=8.61 Hz, 2H), 7.46 (d, J=8.62 Hz, 2H), 2.43 (t, J=7.44 Hz, 2H), 1.6 (p, J=7.37 Hz, 2H), 1.5-1.4 (m, 2H), 1.38-1.26 (m, 4H), 0.92 (t, J=7.36 Hz, 3H); LCMS m/z: 211.

Example 20

4-(4-Piperidin-1-yl-phenylethynyl)-benzonitrile

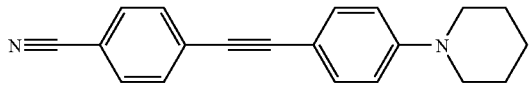 [SMILES: N#Cc1ccc(C#Cc2ccc(N3CCCCC3)cc2)cc1]

This product was prepared from toluene-4-sulfonic acid 4-cyano-phenyl ester and 1-(4-ethynyl-phenyl)-piperazine following the general procedure for the Sonogashira cross-coupling process described above. Chromatography eluent: heptane/EtOAc 9:1; yield (137 mg, 96%); $^1$H NMR δ (CDCl$_3$): 7.61-7.51 (m, 4H), 7.4 (d, J=8.41 Hz, 2H), 6.85 (d, J=8.42 Hz, 2H), 3.25 (m, 4H), 1.73-153 (m, 6H); LCMS m/z 286.

Example 21

4-(3-Diethylamino-prop-1-ynyl)-benzonitrile

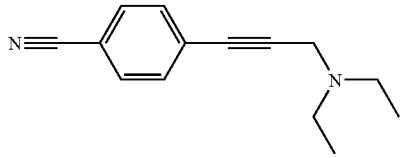 [SMILES: CCN(CC)CC#Cc1ccc(C#N)cc1]

This product was prepared from toluene-4-sulfonic acid 4-cyano-phenyl ester and diethyl-prop-2-ynyl-amine following the general procedure for the Sonogashira cross-coupling process described above. Chromatography eluent: heptane/EtOAc 6:4; yield (95.4 mg, 90%); $^1$H NMR δ (CDCl$_3$): 7.58 (d, J=8.65 Hz, 2H), 7.49 (d, J=8.63 Hz, 2H), 3.64 (s, 2H), 2.61 (q, J=7.16 Hz, 4H), 1.11 (t, J=7.15 Hz, 6H); LCMS m/z: 212.

Example 22

[(4-Hept-1-ynyl)-phenyl)]-acetonitrile

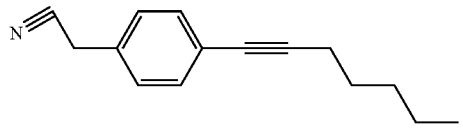

This product was prepared from toluene-4-sulfonic acid 4-cyanomethyl-phenyl ester and 1-heptyne following the general procedure for the Sonogashira cross-coupling process described above. Chromatography eluent: heptane/EtOAc 9:1; yield (90 mg, 85%); $^1$H NMR δ (CDCl$_3$): 7.4 (d, J=8.55 Hz, 2H), 7.23 (d, J=8.53 Hz, 2H), 3.73 (s, 2H), 2.43 (t, J=7.22 Hz, 2H), 1.62 (p, J=7.14 Hz, 2H), 1.48-1.3 (m, 4H), 0.93 (t, J=7.22 Hz, 3H), LCMS m/z: 207.

Example 23

[4-(5-Phenyl-pent-1-ynyl)-phenyl)]-acetonitrile

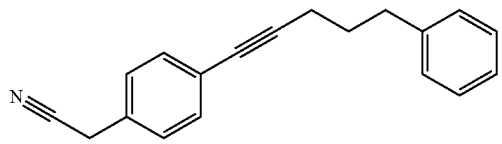 [SMILES: N#CCc1ccc(C#CCCCc2ccccc2)cc1]

This product was prepared from toluene-4-sulfonic acid 4-cyanomethyl-phenyl ester and pent-4-ynyl-benzene following the general procedure for the Sonogashira cross-coupling process described above. Chromatography eluent: heptane/EtOAc 9:1; yield (65 mg, 50%); $^1$H NMR δ (CDCl$_3$): 7.4 (d, J=8.53 Hz, 2H), 7.23 (d, J=8.52 Hz, 2H), 7.57-7.47 (m, 5H), 3.73 (s, 2H), 2.79 (t, J=7.16 Hz, 2H), 2.48 (t, J=7.11 Hz, 2H), 1.93 (p, J=7.20 Hz, 2H); LCMS m/z: 259.

Example 24

1-Hept-1-ynyl-4-trifluoromethoxy-benzene

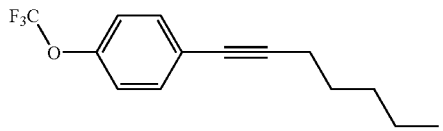

This product was prepared from toluene-4-sulfonic acid 4-trifluoromethoxy-phenyl ester and 1-heptyne following the general procedure for the Sonogashira cross-coupling process described above. Chromatography eluent: heptane; yield (100 mg, 78%); $^1$H NMR δ (CDCl$_3$): 7.41 (d, J=8.55 Hz, 2H), 7.21 (d, J=8.56 Hz, 2H), 2.43 (t, J=7.21 Hz, 2H), 1.62 (p, J=7.16 Hz, 2H), 1.48-1.3 (m, 4H), 0.93 (t, J=7.22 Hz, 3H); LCMS m/z: 256.

Example 25

2-(5-Phenyl-pent-1-ynyl)-4-trifluoromethoxy-benzene

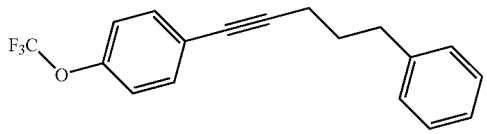 [SMILES: FC(F)(F)Oc1ccc(C#CCCCc2ccccc2)cc1]

This product was prepared from toluene-4-sulfonic acid 4-trifluoromethoxy-phenyl ester and pent-4-ynyl-benzene. Chromatography eluent: heptane; yield (140 mg, 93%); $^1$H NMR δ (CDCl$_3$): 7.41 (d, J=8.32 Hz, 2H), 7.38-7.28 (m, 2H), 7.27-7.18 (m, 3H), 7.21 (d, J=8.34 Hz, 2H), 2.77 (t, J=7.12 Hz, 2H), 2.45 (t, J=7.13 Hz, 2H), 1.93 (p, J=7.21 Hz, 2H); LCMS m/z: 300.

Example 26

1-Cyclohex-1-enylethynyl-4-trifluoromethoxy-benzene

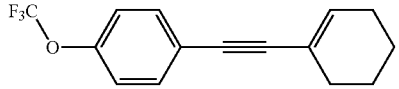

This product was prepared from toluene-4-sulfonic acid 4-trifluoromethoxy-phenyl ester and 1-ethynyl-cyclohexene following the general procedure for the Sonogashira cross-coupling process described above. Chromatography eluent: heptane; yield (110 mg, 83%); $^1$H NMR δ (CDCl$_3$): 7.41 (d, J=8.38 Hz, 2H), 7.21 (d, J=8.37 Hz, 2H), 6.28 (m, 1H), 2.17 (dm, 4H), 1.63 (dm, 4H); LCMS m/z: 266.

Example 27

1,2-Dimethoxy-4-(4-Trifluoromethoxy-phenylethynyl)-benzene

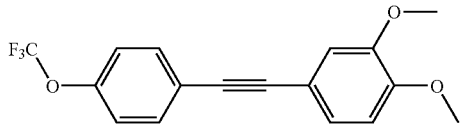

This product was prepared from toluene-4-sulfonic acid 4-trifluoromethoxy-phenyl ester and 4-ethynyl-1,2-dimethoxy-benzene following the general procedure for the Sonogashira cross-coupling process described above. Chromatography eluent: heptane; yield (140 mg, 87%); $^1$H NMR δ (CDCl$_3$): 7.52 (d, J=8.40 Hz, 2H), 7.21-7.16 (m, 3H), 6.83 (d, J=8.41 Hz, 2H), 3.85 (s, 6H); LCMS m/z: 322.

Example 28

4-(4-Trifluoromethoxy-phenylethynyl)-phenylamine

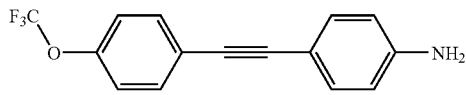 [SMILES: Nc1ccc(C#Cc2ccc(OC(F)(F)F)cc2)cc1]

This product was prepared from toluene-4-sulfonic acid 4-trifluoromethoxy-phenyl ester and 4-ethynyl-phenylamine. Chromatography eluent: heptane; yield (111 mg, 80%); $^1$H NMR δ (CDCl$_3$): 7.5 (d, J=8.42 Hz, 2H), 7.33 (d, J=8.60 Hz, 2H), 7.18 (d, J=8.41 Hz, 2H), 6.62 (d, J=8.62 Hz, 2H), 3.82 (s, 2H); LCMS m/z 277.

Example 29

1-Chloro-3-fluoro-5-hept-1-ynyl-benzene

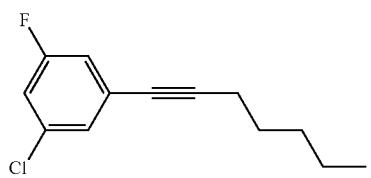

This product was prepared from toluene-4-sulfonic acid 3-chloro-5-fluoro-phenyl ester and 1-heptyne following the general procedure for the Sonogashira cross-coupling process described above. Chromatography eluent: heptane; yield (110 mg, 98%); $^1$H NMR δ (CDCl$_3$): 7.16 (s, 1H), 7.02-6.94 (m, 2H), 2.43 (t, J=7.13 Hz, 2H), 1.62 (p, J=7.12 Hz, 2H), 1.45-1.29 (m, 4H), 0.92 (t, J=7.22 Hz, 3H); LCMS m/z: 224.

Example 30

1-Chloro-3-fluoro-5-phenylethynyl-benzene

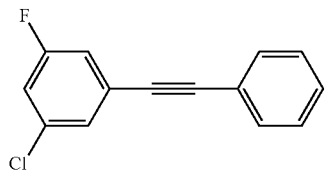 [SMILES: Fc1cc(Cl)cc(C#Cc2ccccc2)c1]

This product was prepared from toluene-4-sulfonic acid 3-chloro-5-fluoro-phenyl ester and ethynyl-benzene following the general procedure for the Sonogashira cross-coupling process described above. Chromatography eluent: heptane; yield (110 mg, 98%); $^1$H NMR δ (CDCl$_3$): 7.51 (m, 2H), 7.36 (m, 3H), 7.03 (d, J=7.05 Hz, 2H), 6.79 (t, J=8.35 Hz, 1H); LCMS m/z: 230.

Example 31

1-Chloro-3-fluoro-5-hept-1-ynyl-benzene

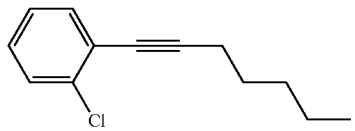

This product was prepared from toluene-4-sulfonic acid 2-chloro-phenyl ester and 1-heptyne following the general procedure for the Sonogashira cross-coupling process described above. Chromatography eluent: heptane; yield (90 mg, 87%); $^1$H NMR δ (CDCl$_3$): 7.43 (d, J=8.53 Hz, 2H), 7.37 (d, J=8.49 Hz, 2H), 2.45 (t, J=7.14 Hz, 2H), 1.63 (p, J=7.12 Hz, 2H), 1.52-1.28 (dm, 4H), 0.92 (t, J=7.22 Hz, 3H); LCMS m/z: 206.

Example 32

1-Chloro-3-fluoro-5-phenylethynyl-benzene

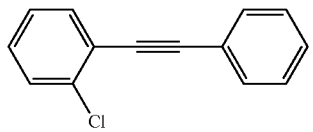 [SMILES: Clc1ccccc1C#Cc1ccccc1]

This product was prepared from toluene-4-sulfonic acid 2-chloro-phenyl ester and ethynyl-benzene following the general procedure for the Sonogashira cross-coupling process described above. Chromatography eluent: heptane; yield (75 mg, 71%); $^1$H NMR δ (CDCl$_3$): 7.62-7.47 (m, 4H), 7.40-7.29 (m, 4H), 7.28-7.19 (m, 1H); LCMS m/z: 212.

Example 33

4-(5-Cyano-pent-1-ynyl)-3-methoxy-benzonitrile

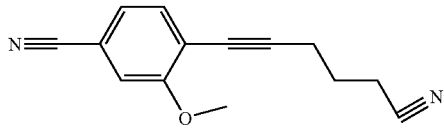 [SMILES: COc1cc(C#N)ccc1C#CCCCC#N]

This product was prepared from benzenesulfonic acid 4-cyano-2-methoxy-phenyl ester and 5-hexynenitrile following the general procedure for the Sonogashira cross-coupling process described above. Chromatography eluent: heptane/EtOAc 8:2; yield (70 mg, 62%); $^1$H NMR δ (CDCl$_3$): 7.52 (d, J=8.34 Hz, 1H), 7.21 (d, J=8.22 Hz, 1H), 7.11 (s, 1H), 3.81 (s, 3H), 2.69 (t, J=7.25 Hz, 2H), 2.58 (t, J=7.22 Hz, 2H), 1.99 (p, J=7.12 Hz, 2H); LCMS m/z: 224.

Example 34

4-(3-Diethylamino-prop-1-ynyl)-3-methoxy-benzonitrile

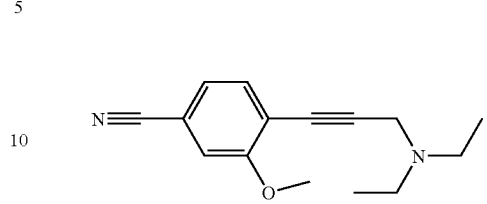

This product was prepared from benzene-sulfonic acid 4-cyano-2-methoxy-phenyl ester and diethyl-prop-2-ynyl-amine following the general procedure for the Sonogashira cross-coupling process described above. Chromatography eluent: heptane/EtOAc 1:1; yield (90 mg, 74%); $^1$H NMR δ (CDCl$_3$): 7.52 (d, J=8.35 Hz, 1H), 7.21 (d, J=8.21 Hz, 1H), 7.11 (s, 1H), 3.81 (s, 3H), 2.69 (t, J=7.22 Hz, 2H), 2.58 (t, J=7.21 Hz, 2H), 1.99 (p, J=7.11 Hz, 2H); LCMS m/z: 242.

Example 35

6-(6-Hydroxy-hex-1-ynyl)-naphtalene-2-carbonitrile

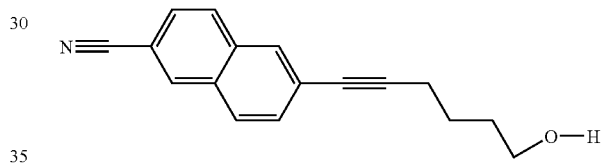

This product was prepared from benzenesulfonic acid 6-cyano-naphthalen-2-yl ester and hex-5-yn-1-ol following the general procedure for the Sonogashira cross-coupling process described above. Chromatography eluent: heptane/EtOAc 6:4; yield (90 mg, 72%); $^1$H NMR δ (CDCl$_3$): 8.2 (s, 1H), 7.93 (s, 1H), 7.88-7.76 (m, 2H), 7.65-7.52 (m, 2H), 3.73 (t, J=7.20 Hz, 2H), 2.50 (t, J=7.22 Hz, 2H), 1.87-1.68 (br m, 5H); LCMS m/z: 249.

Example 36

6-(4-Methoxy-phenylethynyl)-naphthalene-2-carbonitrile

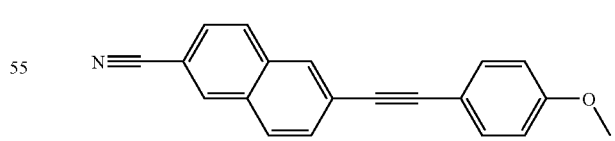

This product was prepared from benzenesulfonic acid 6-cyano-naphthalen-2-yl ester and 1-ethynyl-4-methoxy-benzene following the general procedure for the Sonogashira cross-coupling process described above. Chromatography eluent: heptane/EtOAc 95:5; yield (140 mg, 98%); $^1$H NMR δ (CDCl$_3$): 8.20 (s, 1H), 8.06 (s, 1H), 7.88 (t, J=7.81 Hz, 2H), 7.71-7.59 (dm, 2H), 6.92 (m, 2H), 3.83 (s, 3H); LCMS m/z: 283.

What is claimed is:

1. A process for preparing a compound of formula I

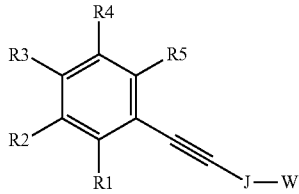

and/or all stereoisomeric forms of the compound of formula I, and/or mixtures of these forms in any ratio, and/or a physiologically tolerated salt of the compound of formula I, wherein J is a covalent bond;
—$(C_1-C_6)$-alkylene, wherein alkylene is unsubstituted or mono-, di- or trisubstituted independently of one another by R6;
—$(C_3-C_8)$-cycloalkyl, wherein cycloalkyl is unsubstituted or mono-, di- or trisubstituted independently of one another by R14;
—$(C_6-C_{14})$-aryl, wherein aryl is unsubstituted or mono-, di-, tri- or four times substituted independently of one another by R13; or
—$(C_4-C_{14})$-heteroaryl, wherein heteroaryl is unsubstituted or mono-, di-, tri- or four times substituted independently of one another by R13;

W is hydrogen atom,
—$(C_1-C_6)$-alkyl, wherein alkyl is unsubstituted or mono-, di- or trisubstituted independently of one another by R6;
—$(C_3-C_8)$-cycloalkyl, wherein cycloalkyl is unsubstituted or mono-, di- or trisubstituted independently of one another by R6;
—$(C_6-C_{14})$-aryl, wherein aryl is unsubstituted or mono-, di-, tri- or four times substituted independently of one another by R6; or
—$(C_4-C_{14})$-heteroaryl, wherein heteroaryl is unsubstituted or mono-, di-, tri- or four times substituted independently of one another by R6;

R1, R2, R3, R4, R5 and R6 are independent of one another identical or different and are
a) hydrogen atom,
b) —$(C_1-C_4)$-alkyl, wherein alkyl is unsubstituted or substituted one to three times by R13,
c) halogen,
d) phenyloxy-, wherein phenyloxy is unsubstituted or substituted one to three times by R13,
e) —$(C_1-C_3)$-fluoroalkyl,
f) —N(R15)-$(C_1-C_4)$-alkyl, wherein alkyl is unsubstituted or substituted one to three times by R13,
g) —$(C_6-C_{14})$-aryl, wherein aryl is unsubstituted or mono-, di-, tri- or four times substituted independently of one another by R13,
h) —$(C_4-C_{14})$-heteroaryl, wherein heteroaryl is unsubstituted or mono-, di-, tri- or four times substituted independently of one another by R13,
i) —$(C_3-C_8)$-cycloalkyl, wherein said cycloalkyl is unsubstituted or mono-, di-, tri- or four times substituted independently of one another by R13,
j) a 3- to 7-membered cyclic residue, containing 1, 2, 3 or 4 heteroatoms chosen from nitrogen, sulfur or oxygen, wherein said cyclic residue is unsubstituted or mono-, di-, tri- or four times substituted independently of one another by R13,
k) —O—$CF_3$,
l) —O—$(C_1-C_4)$-alkyl, wherein alkyl is unsubstituted or substituted one to three times by R13,
m) —$NO_2$,
n) —CN,
o) —OH,
p) —C(O)—R15,
q) —C(O)—O—R16,
r) —C(O)—N(R16)-R12,
s) —N(R16)-R12,
t) —N(R15)-$SO_2$—R15,
v) —S—R15,
w) —$SO_n$—R15, wherein n is 1 or 2,
x) —$SO_2$—N(R16)-R12 or
y) —Si(R16)(R16)-R12, or R1 and R2, R2 and R3, R3 and R4 or R4 and R5 form together with the atoms which they are attached to a 5- or 8-membered ring, containing up to 0, 1, 2, 3 or 4 heteroatoms chosen from nitrogen, sulfur or oxygen, wherein said ring is unsubstituted or substituted one, two, three or four times by R14, R15 is hydrogen atom, —$(C_1-C_3)$-fluoroalkyl or —$(C_1-C_6)$-alkyl, R16 and R12 are independently of one another identical or different and are
a) hydrogen atom,
b) —$(C_1-C_6)$-alkyl, wherein alkyl is unsubstituted or mono-, di- or trisubstituted independently of one another by R13,
c) —C(O)—$(C_1-C_4)$-alkyl,
d) —$(C_6-C_{14})$-aryl-, wherein aryl is unsubstituted or mono-, di- or trisubstituted independently of one another by R13,
e) —$(C_4-C_{14})$-heteroaryl, wherein heteroaryl is unsubstituted or mono-, di- or trisubstituted independently of one another by R13, R13 is halogen, —$NO_2$, —CN, =O, —OH, —$(C_1-C_8)$-alkyl, —$(C_1-C_8)$-alkoxy, —$CF_3$, phenyloxy-, —C(O)—R15, —C(O)—O—R17, —C(O)—N(R17)-R18, —N(R17)-R18, —N(R15)-$SO_2$—R15, —S—R15, —$SO_n$—R15, wherein n is 1 or 2, —$SO_2$—N(R17)-R18-, —$(C_6-C_{14})$-aryl, wherein aryl is unsubstituted or mono-, di- or trisubstituted independently of one another by R14, —$(C_4-C_{14})$-heteroaryl, wherein heteroaryl is unsubstituted or mono-, di- or trisubstituted independently of one another by R14, —$(C_3-C_8)$-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, R14 is halogen, —OH, =O, —CN, —$CF_3$, —$(C_1-C_8)$-alkyl, —$(C_1-C_4)$-alkoxy, —$NO_2$, —C(O)—OH, —CN, —$NH_2$, —C(O)—O—$(C_1-C_4)$-alkyl, —$(C_1-C_8)$-alkylsulfonyl, —C(O)—NH—$(C_1-C_8)$-alkyl, —C(O)—N—$[(C_1-C_8)$-alkyl$]_2$, —C(O)—$NH_2$, —S—R15, —N(R15)-C(O)—NH—$(C_1-C_8)$-alkyl, or —N(R15)-C(O)—N—$[(C_1-C_8)$-alkyl$]_2$, R17 and R18 are independently of one another identical or different and are
a) hydrogen atom,
b) —$(C_1-C_6)$-alkyl, c) —(C$_6$-C$_{14}$)-aryl- or
d) —(C$_4$-C$_{14}$)-heteroaryl,
said process comprises reacting a compound of formula II,

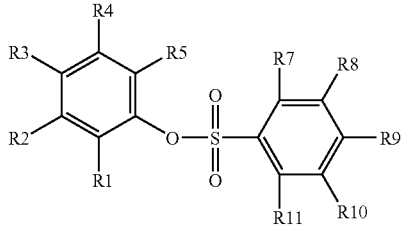

(II)

wherein R1, R2, R3, R4 and R5 are as defined in formula I and
R7, R8, R9, R10 and R11 are
a) hydrogen atom,
b) —(C$_1$-C$_4$)-alkyl,
c) halogen,
d) —(C$_1$-C$_3$)-fluoroalkyl,
e) —O—CF$_3$,
f) —NO$_2$,
g) —CN,
h) —OH,
i) —C(O)—R15,
j) —C(O)—O—R16,
k) —C(O)—N(R16)-R12,
l) —N(R16)-R12,
m) —SO$_n$—R15, wherein n is 1 or 2, or
n) —SO$_2$—N(R16)-R12,
with a compound of formula III

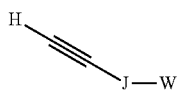

(III)

wherein J, and W are as defined in formula I,
in the presence of a palladium catalyst, a base, a bidentate ligand and a protic solvent to give a compound of formula I and optionally the compound of formula I is converted to its physiologically tolerated salt.

2. The process according to claim 1, wherein a compound of formula I is prepared, wherein
J is a covalent bond;
—(C$_1$-C$_6$)-alkylene, wherein alkylene is unsubstituted or mono-, di- or trisubstituted independently of one another by R6;
—(C$_3$-C$_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; or
—(C$_4$-C$_{14}$)-heteroaryl, wherein heteroaryl is selected from acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and is unsubstituted or mono-, di-, tri- or four times substituted independently of one another by R13;
W is hydrogen atom,
—(C$_1$-C$_6$)-alkyl, wherein alkyl is unsubstituted or mono-, di- or trisubstituted independently of one another by R6,
—(C$_3$-C$_6$)-cycloalkyl, wherein cycloalkyl is unsubstituted or mono-, di- or trisubstituted independently of one another by R6,
phenyl, wherein phenyl is unsubstituted or mono-, di-, tri- or four times substituted independently of one another by R6; or
—(C$_4$-C$_{14}$)-heteroaryl, wherein heteroaryl is as defined above and is unsubstituted or mono-, di-, tri- or four times substituted independently of one another by R6;
R1, R2, R3, R4, R5 and R6 are independent of one another identical or different and are
a) hydrogen atom,
b) —(C$_1$-C$_4$)-alkyl, wherein alkyl is unsubstituted or substituted one to three times by R13,
c) halogen,
d) phenyloxy-, wherein phenyloxy is unsubstituted or substituted one to three times by R13,
e) —(C$_1$-C$_3$)-fluoroalkyl,
f) —N(R15)-(C$_1$-C$_4$)-alkyl, wherein alkyl is unsubstituted or substituted one to three times by R13,
g) phenyl, wherein phenyl is as defined above and is unsubstituted or mono-, di-, tri- or four times substituted independently of one another by R13,
h) —(C$_4$-C$_{14}$)-heteroaryl, wherein heteroaryl is as defined above and is unsubstituted or mono-, di-, tri- or four times substituted independently of one another by R13, i) —($C_3$-$C_8$)-cycloalkyl, wherein said cycloalkyl is unsubstituted or mono-, di-, tri- or four times substituted independently of one another by R13,
j) a 3- to 7-membered cyclic residue is selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxathiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13,
k) —O—$CF_3$,
l) —O—($C_1$-$C_4$)-alkyl, wherein alkyl is unsubstituted or substituted one to three times by R13,
m) —$NO_2$,
n) —CN,
o) —OH,
p) —C(O)—R15,
q) —C(O)—O—R16,
r) —C(O)—N(R16)-R12,
s) —N(R16)-R12,
t) —N(R15)-$SO_2$—R15,
v) —S—R15,
w) —$SO_n$—R15, wherein n is 1 or 2,
x) —$SO_2$—N(R16)-R12 or
y) —Si(R16)(R16)-R12, or
R1 and R2, R2 and R3, R3 and R4 or R4 and R5 form together with the atoms which they are attached to a phenyl ring, wherein phenyl is unsubstituted or substituted by R14,
R15 is hydrogen atom, —($C_1$-$C_3$)-fluoroalkyl or —($C_1$-$C_6$)-alkyl,
R16 and R12 are independently of one another identical or different and are
a) hydrogen atom,
b) —($C_1$-$C_4$)-alkyl, wherein alkyl is unsubstituted or mono-, di- or trisubstituted independently of one another by R13,
c) —C(O)—($C_1$-$C_4$)-alkyl,
d) phenyl, wherein phenyl is unsubstituted or mono-, di- or trisubstituted independently of one another by R13,
e) —($C_4$-$C_{14}$)-heteroaryl, wherein heteroaryl is as defined above and is unsubstituted or mono-, di- or trisubstituted independently of one another by R13,
R13 is F, Cl, —CN, =O, —OH, —($C_1$-$C_8$)-alkyl, —($C_1$-$C_8$)-alkoxy, —$CF_3$, phenyloxy-, —C(O)—R15, —C(O)—O—R17, —C(O)—N(R17)-R18, —N(R17)-R18, —N(R15)-$SO_2$—R15, —S—R15, —$SO_n$—R15, wherein n is 1 or 2, —$SO_2$—N(R17)-R18, phenyl, wherein phenyl is unsubstituted or mono-, di- or trisubstituted independently of one another by R14, —($C_4$-$C_{14}$)-heteroaryl, wherein heteroaryl is as defined above and is unsubstituted or mono-, di- or trisubstituted independently of one another by R14, —($C_3$-$C_6$)-cycloalkyl, wherein said cycloalkyl is unsubstituted or mono-, di- or trisubstituted independently of one another by R14, or a 3- to 7-membered cyclic residue, which is as defined above and is unsubstituted or mono-, di- or trisubstituted independently of one another by R14,
R14 is F, Cl, —OH, =O, —CN, —$CF_3$, —($C_1$-$C_8$)-alkyl, —($C_1$-$C_4$)-alkoxy, —C(O)—OH, —CN, —$NH_2$, —C(O)—O—($C_1$-$C_4$)-alkyl, —($C_1$-$C_8$)-alkylsulfonyl, —C(O)—$NH_2$, —C(O)—NH—($C_1$-$C_8$)-alkyl, —C(O)—N—[($C_1$-$C_8$)-alkyl]$_2$, —S—R15, —N(R15)-C(O)—NH—($C_1$-$C_8$)-alkyl or —N(R15)-C(O)—N—[($C_1$-$C_8$)-alkyl]$_2$,
R17 and R18 are independently of one another identical or different and are
a) hydrogen atom,
b) —($C_1$-$C_4$)-alkyl,
c) phenyl or
d) —($C_4$-$C_{14}$)-heteroaryl, wherein heteroaryl is as defined above, and
R7, R8, R9, R10 and R11 are
a) hydrogen atom,
b) —($C_1$-$C_4$)-alkyl,
c) halogen,
d) —($C_1$-$C_3$)-fluoroalkyl,
e) —O—$CF_3$,
f) —$NO_2$,
g) —CN,
h) —OH,
i) —C(O)—R15,
j) —C(O)—O—R16,
k) —C(O)—N(R16)-R12,
l) —N(R16)-R12,
m) —$SO_n$—R15, wherein n is 1 or 2, or
n) —$SO_2$—N(R16)-R12.

3. The process according to claim 1, wherein a compound of formula I is prepared, wherein
J is a covalent bond, —($C_1$-$C_6$)-alkylene, wherein alkylene is unsubstituted or mono- or disubstituted independently of one another by R6, cyclohexenyl, cyclohexyl, phenyl, wherein phenyl is unsubstituted or mono- or disubstituted independently of one another by R13 or thienyl,
W is hydrogen atom, —($C_1$-$C_4$)-alkyl, wherein alkyl is unsubstituted or mono- or disubstituted independently of one another by R6, cyclohexenyl, cyclohexyl, phenyl, wherein phenyl is unsubstituted or mono- or disubstituted independently of one another by R6 or piperidinyl,
R1, R2, R3, R4, R5 and R6 are independent of one another identical or different and are
a) hydrogen atom,
b) —($C_1$-$C_4$)-alkyl, wherein alkyl is unsubstituted or substituted one time by R13,
c) fluorine,
d) chlorine,
e) —$CF_3$,
f) —N(R15)-($C_1$-$C_4$)-alkyl,
g) —O—$CF_3$,
h) —O—($C_1$-$C_4$)-alkyl,
i) —CN,
j) —OH,
k) —C(O)—R15,
l) —C(O)—O—R16, or
m) —N(R16)-R12, or
R1 and R2, R2 and R3, R3 and R4 or R4 and R5 form together with the atoms which they are attached to a phenyl ring, wherein phenyl is unsubstituted or substituted by —CN,
R15 is hydrogen atom or —($C_1$-$C_4$)-alkyl, R16 and R12 are independently of one another identical or different and are
a) hydrogen atom,
b) —($C_1$-$C_4$)-alkyl, or
c) —C(O)—($C_1$-$C_4$)-alkyl,
R13 is F, Cl, —CN or —N(R17)-R18,
R14 is F, Cl or —CN,
R17 and R18 are independently of one another identical or different and are hydrogen atom or —($C_1$-$C_4$)-alkyl, and
R7, R8, R9, R10 and R11 are independently of one another identical or different and are hydrogen atom or methyl.

4. The process according to claim 1, wherein one of the following compounds of formula I is prepared:
N-(2-Hept-1ynyl-phenyl)-acetamide, N-(2-Cyclohex-1-enylethynyl-phenyl)-acetamide, N-(2-Thiophen-3-yl-ethynyl-phenyl)-acetamide, N-(2-Phenylethynyl-phenyl)-acetamide, N-[2-(4-Amino-phenylethynyl)-phenyl]-acetamide, N-[2-(3-Diethylamino-prop-1-ynyl)-phenyl]-acetamide, 4-(3-Diethylamino-prop-1-ynyl)-3-methyl-benzoic acid ester, 3-Acetylamino-4-hept-1-ynyl-benzoic acid methyl ester, 1-(4-Hept-1-ynyl-3-methoxy-phenyl)ethanone, 1-(−3-Methoxy-4-(5-phenyl-pent-1-ynyl)-ethanone, 1-(4-Cyclohex-1-enylethynyl-3-methoxy-phenyl)-ethanone, 1-[−4-(3,4-Dimethoxy-phenylethynyl)-3-methoxy-phenyl]-ethanone, 1-(5-Phenyl-pent-1-ynyl)-3-trifluoromethyl-benzene, 1-Cyclohexylethynyl-3-trifluoromethyl-benzene, 1-Cyclohex-1-enylethynyl-3-trifluoromethyl-benzene, 4-(5-Phenyl-pent-1-ynyl)-benzaldehyde, 4-Hept-1-ynyl-benzaldehyde, 4-Cyclohex-1-enylethynyl-benzaldehyde, 4-Hex-1-ynyl-benzonitrile, 4-(4-Pipreidin-1yl-phenylethynyl)-benzonitrile, 4-(3-Diethylamino-prop-1-ynyl)-benzonitrile, [(4-Hept-1-ynyl)-phenyl)]-acetonitrile, [4-(5-Phenyl-pent-1-ynyl)-phenyl)]-acetonitrile, 1-Hept-1-ynyl-4-trifluoromethoxy-benzene, 2-(5-Phenyl-pent-1-ynyl)-4-trifluoromethoxy-benzene, 1-Cyclohex-1-enylethynyl-4-trifluoromethoxy-benzene, 1,2-Dimethoxy-4-(4-Trifluoromethoxy-phenylethynyl)-benzene, 4-(4-Trifluoromethoxy-phenylethynyl)-phenylamine, 1-Chloro-3-fluoro-5-hept-1-ynyl-benzene, 1-Chloro-3-fluoro-5-phenylethynyl-benzene, 1-Chloro-3-fluoro-5-hept-1-ynyl-benzene, 1-Chloro-3-fluoro-5-phenylethynyl-benzene, 4-(5-Cyano-pent-1-ynyl)-3-methoxy-benzonitrile, 4-(3-Diethylamino-prop-1-ynyl)-3-methoxy-benzonitrile, 6-(6-Hydroxy-hex-1-ynyl)-naphtalene-2-carbonitrile or 6-(4-Methoxy-phenylethynyl)-naphtalene-2-carbonitrile.

5. The process according to claim 1, wherein the palladium catalyst is selected from: Pd-alkanoates, Pd-alkanoate complexes, Pd-acetonates, Pd-halides, Pd-halide complexes and Pd-phosphine complexes, provided that the catalyst contains no monophosphino-biphenyl derivative as a ligand.

6. The process according to claim 5, wherein the palladium catalyst is selected from: palladium (II) acetate, palladium (II) trifluoroacetate, palladium (II) hexafluoroacetylacetonate, palladium (II) bromide, palladium (II) chloride, palladium (II) iodide, palladium (II) nitrate, palladium (II) acetylacetonate, dichloro-bis-acetonitrile palladium (II), tetrakis (triphenylphosphine)palladium (0), trans-di(μ-acetato)bis[o-(di-o-tolylphosphino)benzyl]dipalladium (II), tris (dibenzylideneacetone)dipalladium(0), tris (dibenzylideneacetone)-dipalladium(0) chloroform adduct, palladium (II) chloride, 2,2'-bis(diphenylphosphino)-1,1'-binaphthylpalladium(II) chloride, acetato(2'-di-tert-butylphosphino-1,1'-biphenyl-2-yl)palladium(II), (1,2-Bis(diphenylphosphino)-ethane)dichloropalladium(II), Bis[1,2-bis (diphenyl-phosphino)ethane]palladium (0), [(2S,3S)-Bis (diphenylphosphino)butane][eta3-allyl]palladium(II) perchlorate, 1,3-bis(2,4,6-trimethylphenyl)imidazol-2-ylidene(1,4-naphthoquinone)palladium (0) dimer, [P,P'-1,3-bis(di-1-propylphosphino)propane][P-1,3-bis(di-1-propylphosphino)propane]palladium (0), 2-(dimethylamino) ferrocen-1-yl-palladium(II) chloride dinorbornylphosphine complex, chloro(di-2-norbornylphosphino)(2-dimethylaminomethylferrocen-1-yl)palladium (II), 1,1'-bis(diphenylphosphino)ferrocene palladium (II) chloride, dichloro[1,1'-bis(diphenylphosphino)ferrocene]palladium (II) dichloromethane adduct, dichloro((S)—N,N-dimethyl-1-((R)-2-(diphenylphosphino)ferrocenyl)-ethylamine)palladium, (1,1'-bis(diphenylphosphino)ferrocene)palladium(II) chloride, [(2S)-1-[(1S)-1-[bis(1,1-dimethylethyl)phosphino-kappaP]ethyl]-2-(diphenylphosphino-kappaP)ferrocene] palladium dichloride, [(2S)-1-[(1S)-1-[bis(1,1-dimethylethyl)phosphino-kappaP]ethyl]-2-(diphenylphosphino-kappaP)ferrocene][tris(2-methylphenyl)phosphine] palladium, [(2R)-1-[(1R)-1-[bis(1,1-dimethylethyl) phosphino-kappaP]ethyl]-2-(dicyclohexylphosphino-kappaP)ferrocene][tris(2-methylphenyl)phosphine] palladium.

7. The process according to claim 5, wherein the palladium catalyst is palladium (II) acetate, dichloro-bis-acetonitrile palladium (II), palladium (II) bromide, palladium (II) iodide, palladium (II) acetate, palladium (II) trifluoroacetate, tris-(dibenzylideneacetone)dipalladium(0), palladium (II) chloride1-[1-bis(1,1-dimethylethyl)phosphino-kappaP]ethyl]-2-(diphenylphosphino-kappaP)ferrocene]palladium dichloride, 1-[1-[bis(1,1-dimethylethyl)-phosphino-kappaP] ethyl]-2-(diphenylphosphino-kappaP)ferrocene][tris(2-methylphenyl)phosphine]palladium, [1-[(1-[bis(1,1-dimethylethyl)phosphino-kappaP]ethyl]-2-(dicyclohexylphosphino-kappaP)ferrocene][tris(2-methylphenyl)phosphine] palladium, or palladium (II) trifluoroacetate.

8. The process according to claim 1, wherein the base is selected out of the group of carbonates, phosphates, fluorides, alkoxides and hydroxides with a suitable metal as counter ion.

9. The process according to claim 8, wherein the base is selected out of the group: potassium carbonate, potassium phosphate and caesium carbonate.

10. The process according to claim 1, wherein the bdentate ligand is selected out of the group: (+/−)-2,2'-bis(diphenylphosphino)-1,1'-binaphthalene, (9,9-dimethyl-9h-xanthene-4,5-diyl)bis[diphenyl phosphine], (R)-(−)-1-[(S)-2-(diphenylphosphino) ferrocenyl] ethyldicyclohexylphosphine, 1,2-Bis(diphenylphosphino) ethane, (2S,3S)-(−)-bis(diphenylphosphino)butane, 1,3-Bis (diphenylphosphino)propane, (R)-(−)-1-[(S)-2-(Dicyclohexylphosphino) ferrocenyl]-ethyldi-tert-butylphosphine, (R)-(+)-1,1'-Bis(diphenylphosphino)-2,2'-bis(N,N-diisopropylamido)ferrocene, (S,S)-1-[1-(Di-tert-butylphosphino)ethyl]-2-(diphenylphosphino)ferrocene, (1R,2R)-(+)-1,2-Diaminocyclohexane-N,N'-bis(2-diphenylphosphino-1-naphtoyl, (−)-1,2-Bis((2S,5S)-2,5-diisopropylpholano)-benzene, Bis[(2-diphenylphosphino)-phenyl]ether, (S)-(−)-2,2'-Bis(di-para-tolylphosphino)-1,1'-binaphyl, 4,5-Bis(bis(3,5-bis(trifluoromethyl)phenyl)-phosphino)-9,9-dimethylxanthen, (R)-(−)-1-[(S)-2-(di(3,5-bis-trifluoromethyl-phenyl)phosphino)-ferrocenyl]-ethyldicyclohexylphosphine, (R)-(−)-1-[(S)-2-(di(3,5-bis-trifluoromethylphenyl)phosphino)ferrocenyl]ethyldi(3,5-dimethyl-phenyl)-phosphine, 2,2'-bis[(2',4',6'-triisopropyl) dicyclohexylphosphino]-biphenyl, 2,2'-bis(di-tert-butylphosphino)biphenyl, (R)-(+)-1-[(R)-2-(2"-di(3,5-xylyl)-phosphinophenyl)ferrocenyl]ethyldi(3,5-xylyl)

phosphine, (R)-(−)-1-[(S)-2-(bis(3,5-dimethyl-4-methoxyphenyl)phosphino)ferrocenyl]ethyldicyclohexylphosphine, (R)-(+)-1-[(R)-2-(2″-di(3,5-dimethyl-4-methoxyphenyl)phosphino-phenyl)-ferrocenyl]ethyldi(bis-3,5-trifluoromethylphenyl)phosphine, (R)-(−)-1-[(S)-2-(dicyclohexylphosphino)ferrocenyl]ethyldi-t-butylphosphine, (R)-(−)-1-[(S)-2-bis(4-trifluoromethylphenyl)phosphino)ferrocenyl]ethyl-di-t-butylphosphine, (1,1′-ferrocenediyl)phenylphosphine, (R)-(+)-1,1′-bis(diphenylphosphino)-2,2′-bis(N,N-diisopropylamido)ferrocene, 1,2,3,4,5-pentaphenyl-1′-(di-t-butylphosphino) ferrocene, (S)-(+)-1-[(R)-2-(diphenylphosphino)ferrocenyl]ethyldi-t-butylphosphine, (R)-(−)-1-[(S)-2-(diphenylphosphino) ferrocenyl]ethyldi-t-butylphosphine, (S)-(+)-1-[(R)-2-(dicyclohexylphosphino) ferrocenyl]ethyldiphenylphosphine, 1,1′-bis(di-1-propylphosphino)ferrocene, (R)-(−)-1-[(S)-2-(dicyclohexylphosphino)-ferrocenyl] ethyldiphenylphosphine, (S)-(+)-1-[(R)-2-(dicyclohexylphosphino) ferrocenyl] ethyldicyclohexylphosphine, (R)-(−)-1-[(S)-2-(dicyclohexyl-phosphino) ferrocenyl] ethyldicyclohexylphosphine, (R)-(−)-1-[(S)-2-(diphenylphosphino) ferrocenyl] ethyldicyclohexylphosphine, 1,1′-bis(di-tert-butylphosphino)ferrocene, (−)-(R)-1-((S)-2-(diphenylphosphino)ferrocenyl)ethyl methyl ether, (+)-(S)-1-((R)-2-(diphenylphosphino)ferrocenyl)ethyl methyl ether, (+)-(S)—N,N-dimethyl-1-((R)-1′,2-bis(diphenylphosphino) ferrocenyl)-ethylamine, or (+)-(S)—N,N-dimethyl-1-((R)-2-(diphenylphosphino)ferrocenyl)-ethylamine, 1,1′-bis(diphenylphosphino)ferrocene.

11. The process according to claim 10, wherein the bidentate ligand is 1-[2-(dicyclohexylphosphino)ferrocenyl]ethyldi-t-butylphosphine or 1-[2-(diphenylphosphino)ferrocenyl]ethyldi-t-butylphosphine.

12. The process according to claim 1, wherein the protic solvent is selected out of the group: water, methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol and cyclohexanol.

13. The process according to claim 12, wherein the protic solvent is selected out of the group: i-butanol, t-butanol, 2-methylbutan-2-ol, 3-methyl-3-pentanol and 3-ethyl-3-pentanol.

14. The process according to claim 1, wherein the reaction between the compounds of formula II and formula III is carried out in the temperature range from 60° C. to 150° C. preferably from 70° C. to 100° C.

* * * * *